United States Patent
Heller et al.

[11] Patent Number: 6,162,611
[45] Date of Patent: Dec. 19, 2000

[54] SUBCUTANEOUS GLUCOSE ELECTRODE

[75] Inventors: Adam Heller; Michael V. Pishko, both of Austin, Tex.

[73] Assignee: E. Heller & Company, Alameda, Calif.

[21] Appl. No.: 09/477,053

[22] Filed: Jan. 3, 2000

Related U.S. Application Data

[63] Continuation of application No. 09/356,102, Jul. 16, 1999, which is a continuation of application No. 08/767,110, Dec. 4, 1996, which is a continuation of application No. 08/299,526, Sep. 1, 1994, Pat. No. 5,593,852, and a continuation-in-part of application No. 08/161,682, Dec. 2, 1993, Pat. No. 5,356,786.

[51] Int. Cl.⁷ .............................. C12Q 1/54; C12Q 1/28; C12Q 1/00; C12Q 1/26
[52] U.S. Cl. .................... 435/14; 435/28; 435/4; 435/25; 435/289.1; 435/917; 436/63; 436/149
[58] Field of Search ................... 435/14, 28, 4, 435/25, 289.1, 817; 436/63, 149

[56] References Cited

U.S. PATENT DOCUMENTS

| | | | |
|---|---|---|---|
| Re. 32,947 | 6/1989 | Dormer et al. | 435/14 |
| 3,260,656 | 7/1966 | Ross, Jr. | 435/14 |
| 3,653,841 | 4/1972 | Klein | 435/14 |
| 3,719,564 | 3/1973 | Lilly, Jr. et al. | 435/14 |
| 3,775,832 | 12/1973 | Oswin et al. | 435/14 |
| 3,837,339 | 9/1974 | Aisenberg et al. | 435/14 |
| 3,926,760 | 12/1975 | Allen et al. | 435/14 |
| 3,972,320 | 8/1976 | Kalman | 435/14 |
| 3,979,274 | 9/1976 | Newman | 435/14 |
| 4,008,717 | 2/1977 | Kowarski | 435/14 |

(List continued on next page.)

FOREIGN PATENT DOCUMENTS

| | | |
|---|---|---|
| 0 010 375 A1 | 4/1980 | European Pat. Off. . |
| 0 026 995 A1 | 4/1981 | European Pat. Off. . |
| 0 048 090 A2 | 3/1982 | European Pat. Off. . |
| 0 078 636 A1 | 5/1983 | European Pat. Off. . |
| 0 096 288 A1 | 12/1983 | European Pat. Off. . |
| 0 125 139 A2 | 11/1984 | European Pat. Off. . |
| 0 127 958 A2 | 12/1984 | European Pat. Off. . |
| 0 136 362 A1 | 4/1985 | European Pat. Off. . |
| 0 170 375 a2 | 2/1986 | European Pat. Off. . |
| 0 177 743 a2 | 4/1986 | European Pat. Off. . |

(List continued on next page.)

OTHER PUBLICATIONS

Abruña, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Abstract from Korf, J. et al., "Monitoring of Glucose and Lactate Using Microdialysis: Applications in Neonates and Rat Brain", *Developmental Neuroscience*, vol. 15, No. 3–5, pp. 240–246 (1993).

Aisenberg et al., "Blood glucose, level monitoring alarm system," Great Britain Patent GB 1394171, issued May 14, 1975, (Abstract only).

Albery, W. J. et al., "Amperometric Enzyme Electrodes," *Phil. Trans. R. Soc. Lond.* B316:107–119 (1987).

(List continued on next page.)

*Primary Examiner*—Louise N. Leary
*Attorney, Agent, or Firm*—Merchant & Gould P.C.

[57] ABSTRACT

A small diameter flexible electrode designed for subcutaneous in vivo amperometric monitoring of glucose is described. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

49 Claims, 10 Drawing Sheets

U.S. PATENT DOCUMENTS

| | | | |
|---|---|---|---|
| 4,016,866 | 4/1977 | Lawton | 435/14 |
| 4,055,175 | 10/1977 | Clemens et al. | 435/14 |
| 4,059,406 | 11/1977 | Fleet | 435/14 |
| 4,076,596 | 2/1978 | Connery et al. | 435/14 |
| 4,098,574 | 7/1978 | Dappen | 435/14 |
| 4,100,048 | 7/1978 | Pompei et al. | 435/14 |
| 4,151,845 | 5/1979 | Clemens | 435/14 |
| 4,168,205 | 9/1979 | Danninger et al. | 435/14 |
| 4,172,770 | 10/1979 | Semersky et al. | 435/14 |
| 4,178,916 | 12/1979 | McNamara | 435/14 |
| 4,206,755 | 6/1980 | Klein | 435/14 |
| 4,224,125 | 9/1980 | Nakamura et al. | 435/14 |
| 4,241,438 | 12/1980 | Updike et al. | 435/14 |
| 4,247,297 | 1/1981 | Berti et al. | 435/14 |
| 4,340,458 | 7/1982 | Lerner et al. | 435/14 |
| 4,352,960 | 10/1982 | Dormer et al. | 435/14 |
| 4,356,074 | 10/1982 | Johnson | 435/14 |
| 4,365,637 | 12/1982 | Johnson | 435/14 |
| 4,366,033 | 12/1982 | Richter et al. | 435/14 |
| 4,375,399 | 3/1983 | Havas et al. | 435/14 |
| 4,384,586 | 5/1983 | Christiansen | 435/14 |
| 4,390,621 | 6/1983 | Bauer | 435/14 |
| 4,401,122 | 8/1983 | Clark, Jr. | 435/14 |
| 4,404,066 | 9/1983 | Johnson | 435/14 |
| 4,418,148 | 11/1983 | Oberhardt | 435/14 |
| 4,427,770 | 1/1984 | Chen et al. | 435/14 |
| 4,431,004 | 2/1984 | Bessman et al. | 435/14 |
| 4,436,094 | 3/1984 | Cerami | 435/14 |
| 4,440,175 | 4/1984 | Wilkins | 435/14 |
| 4,450,842 | 5/1984 | Zick et al. | 435/14 |
| 4,458,686 | 7/1984 | Clark, Jr. | 435/14 |
| 4,461,691 | 7/1984 | Frank | 435/14 |
| 4,469,110 | 9/1984 | Slama | 435/14 |
| 4,477,314 | 10/1984 | Richter et al. | 435/14 |
| 4,484,987 | 11/1984 | Gough | 435/14 |
| 4,522,690 | 6/1985 | Venkatasetty | 435/14 |
| 4,524,114 | 6/1985 | Samuels et al. | 435/14 |
| 4,526,661 | 7/1985 | Steckhan et al. | 435/14 |
| 4,534,356 | 8/1985 | Papadakis | 435/14 |
| 4,538,616 | 9/1985 | Rogoff | 435/14 |
| 4,543,955 | 10/1985 | Schroeppel | 435/14 |
| 4,545,382 | 10/1985 | Higgins et al. | 435/14 |
| 4,552,840 | 11/1985 | Riffer | 435/14 |
| 4,560,534 | 12/1985 | Kung et al. | 435/14 |
| 4,571,292 | 2/1986 | Liu et al. | 435/14 |
| 4,573,994 | 3/1986 | Fischell et al. | 435/14 |
| 4,581,336 | 4/1986 | Malloy et al. | 435/14 |
| 4,595,011 | 6/1986 | Phillips | 435/14 |
| 4,619,754 | 10/1986 | Niki et al. | 435/14 |
| 4,627,445 | 12/1986 | Garcia et al. | 435/14 |
| 4,627,908 | 12/1986 | Miller | 435/14 |
| 4,633,878 | 1/1987 | Bombardieri | 435/14 |
| 4,637,403 | 1/1987 | Garcia et al. | 435/14 |
| 4,650,547 | 3/1987 | Gough | 435/14 |
| 4,654,197 | 3/1987 | Lilja et al. | 435/14 |
| 4,655,880 | 4/1987 | Liu | 435/14 |
| 4,655,885 | 4/1987 | Hill et al. | 435/14 |
| 4,671,288 | 6/1987 | Gough | 435/14 |
| 4,679,562 | 7/1987 | Luksha | 435/14 |
| 4,680,268 | 7/1987 | Clark, Jr. | 435/14 |
| 4,682,602 | 7/1987 | Prohaska | 435/14 |
| 4,684,537 | 8/1987 | Graetzel et al. | 435/14 |
| 4,685,463 | 8/1987 | Williams | 435/14 |
| 4,703,756 | 11/1987 | Gough et al. | 435/14 |
| 4,711,245 | 12/1987 | Higgins et al. | 435/14 |
| 4,717,673 | 1/1988 | Wrighton et al. | 435/14 |
| 4,721,601 | 1/1988 | Wrighton et al. | 435/14 |
| 4,721,677 | 1/1988 | Clark, Jr. | 435/14 |
| 4,726,378 | 2/1988 | Kaplan | 435/14 |
| 4,726,716 | 2/1988 | McGuire | 435/14 |
| 4,757,022 | 7/1988 | Shults et al. | 435/14 |
| 4,758,323 | 7/1988 | Davis et al. | 435/14 |
| 4,759,371 | 7/1988 | Franetzki | 435/14 |
| 4,759,828 | 7/1988 | Young et al. | 435/14 |
| 4,764,416 | 8/1988 | Ueyama et al. | 435/14 |
| 4,776,944 | 10/1988 | Janata et al. | 435/14 |
| 4,777,953 | 10/1988 | Ash et al. | 435/14 |
| 4,781,798 | 11/1988 | Gough | 435/14 |
| 4,784,736 | 11/1988 | Lonsdale et al. | 435/14 |
| 4,795,707 | 1/1989 | Niiyama et al. | 435/14 |
| 4,796,634 | 1/1989 | Huntsman et al. | 435/14 |
| 4,805,624 | 2/1989 | Yao et al. | 435/14 |
| 4,813,424 | 3/1989 | Wilkins | 435/14 |
| 4,815,469 | 3/1989 | Cohen et al. | 435/14 |
| 4,820,399 | 4/1989 | Senda et al. | 435/14 |
| 4,822,337 | 4/1989 | Newhouse et al. | 435/14 |
| 4,830,959 | 5/1989 | McNeil et al. | 435/14 |
| 4,832,797 | 5/1989 | Vadgama et al. | 435/14 |
| 4,840,893 | 6/1989 | Hill et al. | 435/14 |
| 4,848,351 | 7/1989 | Finch | 435/14 |
| 4,854,322 | 8/1989 | Ash et al. | 435/14 |
| 4,871,351 | 10/1989 | Feingold | 435/14 |
| 4,871,440 | 10/1989 | Nagata et al. | 435/14 |
| 4,874,500 | 10/1989 | Madou et al. | 435/14 |
| 4,890,620 | 1/1990 | Gough | 435/14 |
| 4,894,137 | 1/1990 | Takizawa et al. | 435/14 |
| 4,897,162 | 1/1990 | Lewandowski et al. | 435/14 |
| 4,897,173 | 1/1990 | Nankai et al. | 435/14 |
| 4,909,908 | 3/1990 | Ross et al. | 435/14 |
| 4,911,794 | 3/1990 | Parce et al. | 435/14 |
| 4,917,800 | 4/1990 | Lonsdale et al. | 435/14 |
| 4,919,141 | 4/1990 | Zier et al. | 435/14 |
| 4,919,767 | 4/1990 | Vadgama et al. | 435/14 |
| 4,923,586 | 5/1990 | Katayama et al. | 435/14 |
| 4,927,516 | 5/1990 | Yamaguchi et al. | 435/14 |
| 4,934,369 | 6/1990 | Maxwell | 435/14 |
| 4,935,105 | 6/1990 | Churchouse | 435/14 |
| 4,935,345 | 6/1990 | Guilbeau et al. | 435/14 |
| 4,938,860 | 7/1990 | Wogoman | 435/14 |
| 4,944,299 | 7/1990 | Silvian | 435/14 |
| 4,950,378 | 8/1990 | Nagata | 435/14 |
| 4,953,552 | 9/1990 | DeMarzo | 435/14 |
| 4,954,129 | 9/1990 | Guiliani et al. | 435/14 |
| 4,969,468 | 11/1990 | Byers et al. | 435/14 |
| 4,970,145 | 11/1990 | Bennetto et al. | 435/14 |
| 4,974,929 | 12/1990 | Curry | 435/14 |
| 4,986,271 | 1/1991 | Wilkins | 435/14 |
| 4,994,167 | 2/1991 | Shults et al. | 435/14 |
| 5,001,054 | 3/1991 | Wagner | 435/14 |
| 5,002,054 | 3/1991 | Ash et al. | 435/14 |
| 5,058,592 | 10/1991 | Whisler | 435/14 |
| 5,070,535 | 12/1991 | Hochmair et al. | 435/14 |
| 5,082,550 | 1/1992 | Rishpon et al. | 435/14 |
| 5,082,786 | 1/1992 | Nakamoto | 435/14 |
| 5,089,112 | 2/1992 | Skotheim et al. | 435/14 |
| 5,095,904 | 3/1992 | Seligman et al. | 435/14 |
| 5,101,814 | 4/1992 | Palti | 435/14 |
| 5,106,365 | 4/1992 | Hernandez | 435/14 |
| 5,108,564 | 4/1992 | Szuminsky et al. | 435/14 |
| 5,109,850 | 5/1992 | Blanco et al. | 435/14 |
| 5,120,420 | 6/1992 | Nankai et al. | 435/14 |
| 5,126,034 | 6/1992 | Carter et al. | 435/14 |
| 5,133,856 | 7/1992 | Yamaguchi et al. | 435/14 |
| 5,135,003 | 8/1992 | Souma | 435/14 |
| 5,141,868 | 8/1992 | Shanks et al. | 435/14 |
| 5,161,532 | 11/1992 | Joseph | 435/14 |
| 5,165,407 | 11/1992 | Wilson et al. | 435/14 |
| 5,174,291 | 12/1992 | Schoonen et al. | 435/14 |
| 5,190,041 | 3/1993 | Palti | 435/14 |
| 5,192,416 | 3/1993 | Wang et al. | 435/14 |
| 5,198,367 | 3/1993 | Aizawa et al. | 435/14 |
| 5,202,261 | 4/1993 | Musho et al. | 435/14 |

| Patent No. | Date | Inventor | Class |
|---|---|---|---|
| 5,205,920 | 4/1993 | Oyama et al. | 435/14 |
| 5,208,154 | 5/1993 | Weaver et al. | 435/14 |
| 5,209,229 | 5/1993 | Gilli | 435/14 |
| 5,217,595 | 6/1993 | Smith et al. | 435/14 |
| 5,229,282 | 7/1993 | Yoshioka et al. | 435/14 |
| 5,250,439 | 10/1993 | Musho et al. | 435/14 |
| 5,262,035 | 11/1993 | Gregg et al. | 435/14 |
| 5,262,305 | 11/1993 | Heller et al. | 435/14 |
| 5,264,103 | 11/1993 | Yoshioka et al. | 435/14 |
| 5,264,104 | 11/1993 | Gregg et al. | 435/14 |
| 5,264,106 | 11/1993 | McAleer et al. | 435/14 |
| 5,271,815 | 12/1993 | Wong | 435/14 |
| 5,279,294 | 1/1994 | Anderson et al. | 435/14 |
| 5,286,362 | 2/1994 | Hoenes et al. | 435/14 |
| 5,286,364 | 2/1994 | Yacynych et al. | 435/14 |
| 5,288,636 | 2/1994 | Pollmann et al. | 435/14 |
| 5,293,546 | 3/1994 | Tadros et al. | 435/14 |
| 5,320,098 | 6/1994 | Davidson | 435/14 |
| 5,320,725 | 6/1994 | Gregg et al. | 435/14 |
| 5,322,063 | 6/1994 | Allen et al. | 435/14 |
| 5,337,747 | 8/1994 | Neftel | 435/14 |
| 5,352,348 | 10/1994 | Young et al. | 435/14 |
| 5,356,786 | 10/1994 | Heller et al. | 435/14 |
| 5,368,028 | 11/1994 | Palti | 435/14 |
| 5,372,133 | 12/1994 | Hogen Esch | 435/14 |
| 5,376,251 | 12/1994 | Kaneko et al. | 435/14 |
| 5,378,628 | 1/1995 | Grätzel et al. | 435/14 |
| 5,387,327 | 2/1995 | Khan | 435/14 |
| 5,390,671 | 2/1995 | Lord et al. | 435/14 |
| 5,391,250 | 2/1995 | Cheney, II et al. | 435/14 |
| 5,395,504 | 3/1995 | Sauer et al. | 435/14 |
| 5,411,647 | 5/1995 | Johnson et al. | 435/14 |
| 5,437,999 | 8/1995 | Diebold et al. | 435/14 |
| 5,462,645 | 10/1995 | Albery et al. | 435/14 |
| 5,469,846 | 11/1995 | Khan | 435/14 |
| 5,494,562 | 2/1996 | Maley et al. | 435/14 |
| 5,496,453 | 3/1996 | Uenoyama et al. | 435/14 |
| 5,496,772 | 3/1996 | Schulman et al. | 435/14 |
| 5,531,878 | 7/1996 | Vadgama et al. | 435/14 |
| 5,545,191 | 8/1996 | Mann et al. | 435/14 |
| 5,560,357 | 10/1996 | Faupel et al. | 435/14 |
| 5,565,085 | 10/1996 | Iekda et al. | 435/14 |
| 5,567,302 | 10/1996 | Song et al. | 435/14 |
| 5,568,806 | 10/1996 | Cheney, II et al. | 435/14 |
| 5,569,186 | 10/1996 | Lord et al. | 435/14 |
| 5,582,184 | 12/1996 | Erickson et al. | 435/14 |
| 5,582,697 | 12/1996 | Ikeda et al. | 435/14 |
| 5,582,698 | 12/1996 | Flaherty et al. | 435/14 |
| 5,586,553 | 12/1996 | Halili et al. | 435/14 |
| 5,589,326 | 12/1996 | Deng et al. | 435/14 |
| 5,593,852 | 1/1997 | Heller et al. | 435/14 |
| 5,596,150 | 1/1997 | Arndt et al. | 435/14 |
| 5,617,851 | 4/1997 | Lipkovker | 435/14 |
| 5,628,890 | 5/1997 | Carter et al. | 435/14 |
| 5,651,869 | 7/1997 | Yoshioka et al. | 435/14 |
| 5,660,163 | 8/1997 | Schulman et al. | 435/14 |
| 5,670,031 | 9/1997 | Hintsche et al. | 435/14 |
| 5,680,858 | 10/1997 | Hansen et al. | 435/14 |
| 5,682,233 | 10/1997 | Brinda | 435/14 |
| 5,695,623 | 12/1997 | Michel et al. | 435/14 |
| 5,708,247 | 1/1998 | McAleer et al. | 435/14 |
| 5,711,861 | 1/1998 | Ward et al. | 435/14 |
| 5,711,862 | 1/1998 | Sakoda et al. | 435/14 |
| 5,741,211 | 4/1998 | Renirie et al. | 435/14 |
| 5,791,344 | 8/1998 | Schulman et al. | 435/14 |

FOREIGN PATENT DOCUMENTS

| | | |
|---|---|---|
| 0 080 304 a2 | 5/1986 | European Pat. Off. |
| 0 184 909 a2 | 6/1986 | European Pat. Off. |
| 0 206 218 A2 | 12/1986 | European Pat. Off. |
| 0 230 472 A1 | 8/1987 | European Pat. Off. |
| 0 241 309 A3 | 10/1987 | European Pat. Off. |
| 0 245 073 A2 | 11/1987 | European Pat. Off. |
| 0 278 647 A2 | 8/1988 | European Pat. Off. |
| 0 359 831 A1 | 3/1990 | European Pat. Off. |
| 0 368 209 A1 | 5/1990 | European Pat. Off. |
| 0 390 390 A1 | 10/1990 | European Pat. Off. |
| 0 400 918 A1 | 12/1990 | European Pat. Off. |
| 0 453 283 A1 | 10/1991 | European Pat. Off. |
| 0 470 290 A1 | 2/1992 | European Pat. Off. |
| 0 127 958 B2 | 3/1992 | European Pat. Off. |
| 0 255 291 B1 | 6/1992 | European Pat. Off. |
| 29 03 216 | 8/1979 | Germany. |
| 227 029 A3 | 9/1985 | Germany. |
| 3934299 | 10/1990 | Germany. |
| 44 01 400 A1 | 7/1995 | Germany. |
| 54-41191 | 4/1979 | Japan. |
| 55-10581 | 1/1980 | Japan. |
| 55-10583 | 1/1980 | Japan. |
| 55-10584 | 1/1980 | Japan. |
| 55-12406 | 1/1980 | Japan. |
| 56-163447 | 12/1981 | Japan. |
| 57-70448 | 4/1982 | Japan. |
| 60-173457 | 9/1985 | Japan. |
| 60-173458 | 9/1985 | Japan. |
| 60-173459 | 9/1985 | Japan. |
| 61-90050 | 5/1986 | Japan. |
| 62-85855 | 4/1987 | Japan. |
| 62-114747 | 5/1987 | Japan. |
| 63-58149 | 3/1988 | Japan. |
| 63-128252 | 5/1988 | Japan. |
| 63-139246 | 6/1988 | Japan. |
| 63-294799 | 12/1988 | Japan. |
| 63-317757 | 12/1988 | Japan. |
| 63-317758 | 12/1988 | Japan. |
| 1-114746 | 5/1989 | Japan. |
| 1-114747 | 5/1989 | Japan. |
| 1-124060 | 5/1989 | Japan. |
| 1-134244 | 5/1989 | Japan. |
| 1-156658 | 6/1989 | Japan. |
| 2-62958 | 3/1990 | Japan. |
| 2-120655 | 5/1990 | Japan. |
| 2-287145 | 11/1990 | Japan. |
| 2-310457 | 12/1990 | Japan. |
| 3-26956 | 2/1991 | Japan. |
| 3-28752 | 2/1991 | Japan. |
| 3-202764 | 9/1991 | Japan. |
| 5-72171 | 3/1993 | Japan. |
| 5-196595 | 8/1993 | Japan. |
| 6-190050 | 7/1994 | Japan. |
| 7-72585 | 3/1995 | Japan. |
| 1281988 A1 | 1/1987 | U.S.S.R. |
| 1394171 | 5/1975 | United Kingdom. |
| 1599241 | 9/1981 | United Kingdom. |
| 2 073 891 | 10/1981 | United Kingdom. |
| 2 154 003 | 2/1988 | United Kingdom. |
| 2 204 408 | 11/1988 | United Kingdom. |
| 2 254 436 | 10/1992 | United Kingdom. |
| WO 85/05119 | 11/1985 | WIPO. |
| WO 89/08713 | 9/1989 | WIPO. |
| WO 90/05300 | 5/1990 | WIPO. |
| WO 90/05910 | 5/1990 | WIPO. |
| WO 91/01680 | 2/1991 | WIPO. |
| WO 91/04704 | 4/1991 | WIPO. |
| WO 91/15993 | 10/1991 | WIPO. |
| WO 92/13271 | 8/1992 | WIPO. |
| WO 94/20602 | 9/1994 | WIPO. |
| WO 94/27140 | 11/1994 | WIPO. |
| WO 96/30431 | 10/1996 | WIPO. |
| WO 97/02847 | 1/1997 | WIPO. |
| WO 97/19344 | 5/1997 | WIPO. |
| WO 97/42882 | 11/1997 | WIPO. |
| WO 97/42883 | 11/1997 | WIPO. |
| WO 97/42886 | 11/1997 | WIPO. |

| | | |
|---|---|---|
| WO 97/42888 | 11/1997 | WIPO . |
| WO 97/43962 | 11/1997 | WIPO . |

OTHER PUBLICATIONS

Albery, W. J. et al., "Amperometric enzyme electrodes. Part II. Conducting salts as electrode materials for the oxidation of glucose oxidase," *J. Electroanal. Chem. Interfacial Electrochem.*, 194(2) (1 page—Abstract only) (1985).

Alcock et al., "Continuous Analyte Monitoring to Aid Clinical Practice," *IEEE Engineering in Medicine and Biology*, pp 319–325 (Jun./Jul. 1994).

Anderson, L. B. et al., "Thin–Layer Electrochemistry: Steady–State Methods of Studying Rate Processes," *J. Electroanal. Chem.*, 10:295–395 (1965).

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page—Abstract only) (1990).

Bartlett, P. N. et al., "Strategies for the Development of Amperometric Enzyme Electrodes," *Biosensors*, 3:359–379 (1987/88).

Bindra, D.S. et al., "Design and in Vitro Studies of a Needle–Type Glucose Sensor for Subcutaneous Monitoring", *Anal. Chem.*, 63(17):1692–1696 (Sep. 1, 1991).

Bobbioni–Harsch et al., "Lifespan of subcutaneous glucose sensors and their performances during dynamic glycaemia changes in rats," *J. Biomed. Eng.*, vol. 15, pp. 457–463 (Nov. 1993).

Brandt, J. et al., "Covalent attachment of proteins to polysaccharide carriers by means of benzoquinone," *Biochim. Biophys. Acta*, 386(1) (1 page Abstract only) (1975).

Brownlee, M. et al., "A Glucose–Controlled Insulin–Delivery System: Semisynthetic Insulin Bound to Lectin", *Science*, 206(4423):1190–1191 (Dec. 7, 1979).

Cass, A.E.G. et al., "Ferrocene–Mediated Enzyme Electrode for Amperometric Determination of Glucose", *Anal. Chem.*, 56(4):667–671 (Apr. 1984).

Cass, A.E.G. et al., "Ferricinum Ion As An Electron Acceptor for Oxido–Reductases," *J. Electroanal. Chem.*, 190:117–127 (1985).

Castner, J. F. et al., "Mass Transport and Reaction Kinetic Parameters Determined Electrochemically for Immobilized Glucose Oxidase," *Biochemistry*, 23(10):2203–2210 (1984).

Cerami, "Monitor for continuous in vivo measurement of glucose concentration," United Sates Patent 4,436,094, issued Mar. 13, 1984, 2 pages (Abstract only).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Clark, L.C., Jr. et al., "Electrode Systems for Continuous Monitoring in Cardiovascular Surgery," *Annals New York Academy of Sciences*, pp. 29–45 (1962).

Clark, L.C. et al., "Differential Anodic Enzyme Polarography for the Measurement of Glucose", *Oxygen Transport to Tissue: Instrumentation, Methods, and Physiology*, 127–132 (1973).

Clark, L.C. et al., "Long–term Stability of Electroenzymatic Glucose Sensors Implanted in Mice," *Trans. Am. Soc. Artif. Intern. Organs*, XXXIV:259–265 (1988).

Clarke, W. L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "Design and Optimization of a Selective Subcutaneously Implantable Glucose Electrode Based on "Wired" Glucose Oxidase," *Anal. Chem.* 67(7):1240–1244 (Apr. 1, 1995).

Csöregi, E. et al., "On–Line Glucose Monitoring by Using Microdialysis Sampling and Amperometric Detection Based on "Wired" Glucose Oxidase in Carbon Paste," *Mikrochim. Acta.* 121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme,"*J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosensors," *Ann. Biol. clin.*, 47:607–619 (1989).

Ellis, C. D., "Selectivity and Directed Charge Transfer through an Electroactive Metallopolymer Film," *J. Am. Chem. Soc.*, 103(25):7480–7483 (1981).

Engstrom, R.C., "Electrochemical Pretreatment of Glassy Carbon Electrodes", *Anal. Chem.*, 54(13):2310–2314 (Nov. 1982).

Engstrom, R.C. et al., "Characterization of Electrochemically Pretreated Glassy Carbon Electrodes", *Anal. Chem.*, 56(2):136–141 (Feb. 1984).

Feldman, B.J. et al., "Electron Transfer Kinetics at Redox Polymer/Solution Interfaces Using Microelectrodes and Twin Electrode Thin Layer Cells", *J. Electroanal. Chem.*, 194(1):63–81 (Oct. 10, 1985).

Fischer, H. et al., "Intramolecular Electron Transfer Mediated by 4,4'–Bipyridine and Related Bridging Groups", *J. Am. Chem. Soc.*, 98(18):5512–5517 (Sep. 1, 1976).

Flentge, F. et al., "An Enzyme–Reactor for Electrochemical Monitoring of Choline and Acetylcholine: Applications in High–Performance Liquid Chromatography, Brain Tissue, Microdialysis and Cerebrospinal Fluid", *Analytical Biochemistry*, vol. 204, No. 2, pp. 305–310 (Aug. 1, 1992).

Foulds, N.C. et al., "Enzyme Entrapment in Electrically Conducting Polymers," *J. Chem. Soc., Faraday Trans 1.*, 82:1259–1264 (1986).

Foulds, N.C. et al., "Immobilization of Glucose Oxidase in Ferrocene–Modified Pyrrole Polymers," *Anal. Chem.*, 60(22):2473–2478 (Nov. 15, 1988).

Franetzki, "Implantable, calibrateable measuring instrument for a body substance and a calibrating method," United States Patent 4,759,371, issued Jul. 26, 1988, 2 pages (Abstract only).

Frew, J.E. et al., "Electron–Transfer Biosensors", *Phil. Trans. R. Soc. Lond.,* B316:95–106 (1987).

Gilli, "Apparatus and method employing plural electrode configurations for cardioversi on of atrial fibrillation in an arrhythmia control system," United States Patent 5,209,229, issued May 11, 1993, 2 pgs (Abstract only).

Gorton, L. et al., "Selective detection in flow analysis based on the combination of immobilized enzymes and chemically modified electrodes," *Analytica Chimica Acta.,* 250:203–248 (1991).

Gregg, B. A. et al., "Cross–Linked Redox Gels Containing Glucose Oxidase for Amperometric Biosensor Applications," *Analytical Chemistry,* 62(3):258–263 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.,* 95(15):5970–5975 (1991).

Hale, P.D. et al., "A New Class of Amperometric Biosensor Incorporating a Polymeric Electron–Transfer Mediator," *J. Am. Chem. Soc.,* 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.,* 60(19):2002–2007 (Oct. 1, 1988).

Hawkridge, F. M. et al., "Indirect Coulometric Titration of Biological Electron Transport Components," *Analytical Chemistry,* 45(7):1021–1027 (Jun. 1973).

Heller, A., "Amperometric biosensors based on three–dimensional hydrogel–forming epoxy networks," *Sensors and Actuators B,* 13–14:180–183 (1993).

Heller, A., "Electrical Wiring of Redox Enzymes," *Acc. Chem. Res.,* 23(5):129–134 (1990).

Heller, A., "Electrical Connection of Enzyme Redox Centers to Electrodes," *J. Phys. Chem.,* 96(9):3579–3587 (1992).

Ianniello, R.M. et al., "Differential Pulse Voltammetric Study of Direct Electron Transfer in Glucose Oxidase Chemically Modified Graphite Electrodes", *Anal. Chem.,* 54:(7):1098–1101 (Jun. 1981).

Ianniello, R.M. et al. "Immobilized Enzyme Chemically Modified Electrode as an Amperometric Sensor", *Anal. Chem.,* 53(13):2090–2095 (Nov. 1981).

Ikeda, T. et al., "Kinetics of Outer–Sphere Electron Transfers Between Metal Complexes in Solutions and Polymeric Films on Modified Electrodes", *J. Am. Chem. Soc.,* 103(25):7422–7425 (Dec. 16, 1981).

Ikeda, T. et al., "Glucose oxidase–immobilized benzoquinone–carbon paste electrode as a glucose sensor," *Agric. Biol. Chem.,* 49(2) (1 page—Abstract only) (1985).

Johnson, J.M. et al., "Potential–Dependent Enzymatic Activity in an Enzyme Thin–Layer Cell," *Anal. Chem.* 54:1377–1383 (1982).

Johnson, K.W., "Reproducible Electrodeposition of Biomolecules for the Fabrication of Miniature Electroenzymatic Biosensors", *Sensors and Actuators B Chemical,* B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors,* 1:355–368 (1985).

Josowicz, M. et al., "Electrochemical Pretreatment of Thin Film Platinum Electrodes", *J. Electrochem. Soc.,* 135(1):112–115 (Jan. 1988).

Katakis, I. et al., "L–α–Glycerophosphate and L–Lactate Electrodes Based on the Electrochemical "Wiring" of Oxidases," *Analytical Chemistry,* 64(9):1008–1013 (May 1, 1992).

Katakis, I. et al., "Electrostatic Control of the Electron Transfer Enabling Binding of Recombinant Glucose Oxidase and Redox Polyectrolytes," *J. Am. Chem. Soc.,* 116(8):3617–3618 (1994).

Kenausis, G. et al., "'Wiring' of glucose oxidase and lactate oxidase within a hydrogel made with poly(vinyl pyridine) complexed with $[Os(4,4'–dimethoxy–2,2'–bipyridine)_2Cl]^{+/2+}$," *J. Chem. Soc., Faraday Trans.,* 92(20):4131–4136 (1996).

Klein, "Method and apparatus for the control and regulation of glycemia," United States Patent 4,206,755, issued Jun. 10, 1980, 2 pages (Abstract only).

Klein, "Control and regulation device for glycemia," Great Britain Patent 1599241A, issued Sep. 30, 1981 (Abstract only).

Koudelka, M. et al., "In–Vivo Behaviour of Hypodermically Implanted Microfabricated Glucose Sensors", *Biosensors & Bioelectronics,* 6(1):31–36 (1991).

Kulys, J. et al., "Mediatorless peroxidase electrode and preparation of bienzyme sensors," *Bioelectrochemistry and Bioenergetics,* 24:305–311 (1990).

Lager, W. et al., "Implantable Electrocatalytic Glucose Sensor," *Horm. Metab. Res.,* 26:526–530 (Nov. 1994).

Laurell, T., "A Continuous Glucose Monitoring System Based on Microdialysis", *Journal of Med. Eng. & Tech.,* vol. 16, No. 5, pp. 187–193 (Sep./Oct. 1992).

Lawton, "Implantable electrochemical sensor," United States Patent 4,016,866, issued Apr. 12, 1977, 2 pages (Abstract only).

Lindner, E. et al. "Flexible (Kapton–Based) Microsensor Arrays of High Stability for Cardiovascular Applications",*J. Chem. Soc.Faraday Trans.,* 89(2):361–367 (Jan. 21, 1993).

Maidan, R. et al., "Elimination of Electrooxidizable Interferant–Produced Currents in Amperometric Biosensors," *Analytical Chemistry,* 64(23):2889–2896 (Dec. 1, 1992).

Marko–Varga, G. et al., "Enzyme–Based Biosensor as a Selective Detection Unit in Column Liquid Chromatography", *Journal of Chromatography* A, vol. 660, pp. 153–167 (1994).

Mastrototaro, J.J. et al., "An Electroenzymatic Glucose Sensor Fabricated on a Flexible Substrate", *Sensors and Biosensors B Chemical,* B5:139–144 (1991).

McNeil, C. J. et al., "Thermostable Reduced Nicotinamide Adenine Dinucleotide Oxidase: Application to Amperometric Enzyme Assay," *Anal. Chem.,* 61(1):25–29 (Jan. 1, 1989).

Miyawaki, O. et al., "Electrochemical and Glucose Oxidase Coenzyme Activity of Flavin Adenine Dinculeotide Covalently Attached to Glassy Carbon at the Adenine Amino Group", *Biochimica et Biophysica Acta,* 838:60–68 (1985).

Moatti–Sirat, D. et al., "Towards continuous glucose monitoring: in vivo evaluation of a miniaturized glucose sensor implanted for several days in rat subcutaneous tissue," (1 page—Abstract only) *Diabetologia* 35(3):224–30 (Mar. 1992).

Moatti–Sirat, D. et al., "Evaluating in vitro and in vivo the interference of ascorbate and acetaminophen on glucose detection by a needle–type glucose sensor," *Biosensors & Bioelectronics*, 7(5):345–352 (1992).

Moatti–Sirat, D. et al., "Reduction of acetaminophen interference in glucose sensors by a composite Nafion membrane: demonstration in rats and man," (1 page—Abstract only) *Diabetologia* 37(6):610–6 (Jun. 1994).

Nagy, G. et al., "A New Type of Enzyme Electrode: The Ascorbic Acid Eliminator Electrode," *Life Sciences*, 31(23):2611–2616 (1982).

Nakamura, S. et al., "Effect of Periodate Oxidation on the Structure and Properties of Glucose Oxidase," *Biochimica et Biophysica Acta.*, 445:294–308 (1976).

Narazimhan, K. et al., "p–Benzoquinone activation of metal oxide electrodes for attachment of enzymes," *Enzyme Microb. Technol.*, 7(6) (1 page—Abstract only) (1985).

Ohara, T. J. et al., "Glucose Electrodes Based on Cross–Linked $[Os(bpy)_2Cl]^{+/2+}$ Complexed Poly(1–vinylimadazole) Films," *Analytical Chemistry*, 65(23):3512–3516 (Dec. 1, 1993).

Ohara, T. J. et al., ""Wired" Enzyme Electrodes for Amperometric Determination of Glucose or Lactate in the Presence of Interfering Substances," *Analytical Chemistry*, 66(15):2451–2457 (Aug. 1, 1994).

Ohara, T. J., "Osmium Bipyridyl Redox Polymers Used in Enzyme Electrodes," *Platinum Metals Rev.*, 39(2):54–62 (Apr. 1995).

Olievier, C. N. et al., "In vivo Measurement of Carbon Dioxide Tension with a Miniature Electrode," *Pflugers Arch.* 373:269–272 (1978).

Paddock, R. et al., "Electrocatalytic reduction of hydrogen peroxide via direct electron transfer from pyrolytic graphite electrodes to irreversibly adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Pankratov, I. et al., "Sol–gel derived renewable–surface biosensors," *Journals of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J. "Developing glucose sensors for in vivo use," *TIBTECH*, vol. 11, pp. 285–289 (Jul. 1993).

Pickup, J. et al., "Potentially–implantable, amperometric glucose sensors with mediated electron transfer: improving the operating stability," *Biosensors*, 4(2), 109–19, (Abstract only) (1989).

Pickup, J.C. et al., "In vivo molecular sensing in diabetes mellitus: an implantable glucose sensor with direct electron transfer," *Diabetologia*, 32(3):213–217 (1989).

Pishko, M.V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V. et al., "In vitro and in vivo evaluation in dogs of a miniaturized glucose sensor," *ASAIO Transactions*, 37(3) (1 page—Abstract only) (Jul.–Sep. 1991).

Poitout, V. et al., "Calibration in dogs of a subcutaneous miniaturized glucose sensor using a glucose meter for blood glucose determination," *Biosensors & Bioelectronics*, 7, pp. 587–592 (1992).

Poitout, V. et al., "A glucose monitoring system for on line estimation in man of blood glucose concentration using a miniaturized glucose sensor implanted in the subcutaneous tissue and a wearable control unit," (1 page—Abstract only) *Diabetologia* 36(7):658–63 (Jul. 1993).

Pollak, A. et al., "Enzyme Immobilization by Condensation Copolymerization into Cross–Linked Polyacrylamide Gels," *J. Am. Chem. Soc.*, 102(20):6324–6336 (1980).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sakakida, M. et al., "Ferrocene–mediate needle–type glucose sensor covered with newly designed biocompatible membrane," *Sensors and Actuators B*, 13–14:319–322 (1993).

Samuels, G. J. et al., "An Electrode–Supported Oxidation Catalyst Based on Ruthenium (IV). pH "Encapsulation" in a Polymer Film," *J. Am. Chem. Soc.*, 103(2):307–312 (1981).

Sasso, S.V. et al., "Electropolymerized 1,2–Diaminobenzene as a Means to Prevent Interferences and Fouling and to Stabilize Immobilized Enzyme in Electrochemical Biosensors", *Anal. Chem.*, 62(11):1111–1117 (Jun. 1, 1990).

Scheller, F. et al., "Enzyme electrodes and their application," *Phil. Trans. R. Soc. Lond.*, B 316:85–94 (1987).

Schmehl, R.H. et al., "The Effect of Redox Site Concentration on the Rate of Mediated Oxidation of Solution Substrates by a Redox Copolymer Film", *J. Electroanal. Chem.*, 152:97–109 (Aug. 25, 1983).

Schmidt, F.J. et al., "Calibration of a Wearable Glucose Sensor", *The International Journal of Artificial Organs*, vol. 15, No. 1, pp. 55–61 (1992).

Shichiri, M. et al., "Glycaemic Control in Pancreatetomized Dogs with a Wearable Artificial Endocrine Pancreas", *Diabetologia*, 24(3):179–184 (Mar. 1983).

Sittampalam, G. et al., "Surface–Modified Electrochemical Detector for Liquid Chormatography", *Anal. Chem.*, 55(9):1608–1610 (Aug. 1983).

Soegijoko, S. et al., *Horm. Metab. Res., Suppl. Ser.*, 12, pp. 165–169 (1982) (Abstract).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis*, 8(6):539–543 (1996).

Sternberg, F. et al., "Calibration Problems of Subcutaneous Glucosensors when Applied "In–Situ" in Man," *Horm. metabl. Res*, 26:524–525 (1994).

Sternberg, R. et al., "Covalent Enzyme Coupling on Cellulose Acetate Membranes for Glucose Sensor Development," *Analytical Chemistry*, 60(24):2781–2786 (Dec. 15, 1988).

Sternberg, R. et al., "Study and Development of Multilayer Needle–type Enzyme–based Glucose Microsensors," *Biosensors*, 4:27–40 (1988).

Suekane, M., "Immobilization of glucose isomerase," *Zeitschrift für Allgemeine Mikrobiologie*, 22(8):565–576 (1982).

Tajima, S. et al., "Simultaneous Determination of Glucose and 1,5–Anydroglucitol", *Chemical Abstracts*, 111(25):394 111:228556g (Dec. 18, 1989).

Tarasevich, M.R. "Bioelectrocatalysis", *Comprehensive Treatise of Electrochemistry*, 10 (Ch.4):231–295 (1985).

Tatsuma, T. et al., "Enzyme Monolayer– and Bilayer–Modified Tin Oxide Electrodes for the Determination of Hydrogen Peroxide and Glucose," *Anal. Chem.*, 61(21):2352–2355 (Nov. 1, 1989).

Taylor, C. et al., "'Wiring' of glucose oxidase within a hydrogel made with polyvinyl imidazole complexed with [(Os–4,4'–dimethoxy–2,2'–bipyridine)C1]$^{+/2+}$," *Journal of Electroanalytical Chemistry*, 396:511–515 (1995).

Trojanowicz, M. et al., "Enzyme Entrapped Polypyrrole Modified Electrode for Flow–Injection Determination of Glucose," *Biosensors & Bioelectronics*, 5:149–156 (1990).

Turner, A.P.F. et al., "Diabetes Mellitus: Biosensors for Research and Management", *Biosensors*, 1:85–115 (1985).

Turner, R. F. B. et al., "A Biocompatible Enzyme Electrode for Continuous in vivo Glucose Monitoring in Whole Blood," *Sensors and Actuators*, B1(1–6):561–564 (Jan. 1990).

Tuzhi, P. et al., "Constant Potential Pretreatment of Carbon Fiber Electrodes for In Vivo Electrochemistry", *Analytical Letters*, 24(6):935–945 (1991).

Umaha, M., "Protein–Modified Electrochemically Active Biomaterial Surface," *U.S. Army Research Office Report*, (12 pages) (Dec. 1988).

Urban, G. et al., "Miniaturized Thin–Film Biosensors Using Covalently Immobilized Glucose Oxidase", *Biosensors & Bioelectronics*, 6(7):555–562 (1991).

Vadgama et al., "Sensor devices," United States Patent 5,531,878, issued Jul. 2, 1996, 2 pages (Abstract only).

Velho et al., "Strategies for calibrating a subcutaneous glucose sensor," *Biomedica Biochimica Acta*, vol. 48, Issue 11–12, pp. 957–964 (1989).

Velho, G. et al., "In Vitro and In Vivo Stability of Electrode Potentials in Needle–Type Glucose Sensors", *Diabetes*, 38(2):164–171 (Feb. 1989).

Von Woedtke, T. et al., "In Situ Calibration of Implanted Electrochemical Glucose Sensors", *Biomed. Biochim. Acta*, 48(11/12):943–952 (1989).

Vreeke, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry*, 64(24):3084–3090 (Dec. 15, 1992).

Vreeke, M. S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers*, 7 pgs. (Jul. 26, 1993).

Wang, D. L. et al., "Miniaturized Flexible Amperometric Lactate Probe," *Analytical Chemistry*, 65(8):1069–1073 (Apr. 15, 1993).

Wang, J. et al., "Activation of Glassy Carbon Electrodes by Alternating Current Electrochemical Treatment", *Analytica Chimica Acta*, 167:325–334 (Jan. 1985).

Wang, J. et al., "Amperometric biosensing of organic peroxides with peroxidase–modified electrodes," *Analytica Chimica Acta*. 254:81–88 (1991).

Wang, J. et al., "Screen–Printable Sol–Gel Enzyme–Containing Carbon Inks," *Analytical Chemistry*, 68(15):2705–2708 (Aug. 1, 1996).

Wang, J. et al., "Sol–Gel–Derived Metal–Dispersed Carbon Composite Amperometric Biosensors," *Electroanalysis*, 9(1):52–55 (1997).

Williams, D.L. et al., "Electrochemical–Enzymatic Analysis of Blood Glucose and Lactate", *Anal. Chem.*, 42(1):118–121 (Jan. 1970).

Wilson, G. S. et al., "Progress toward the Development of an Implantable Sensor for Glucose," *Clinical Chemistry*, 38(9):1613–1617 (1992).

Yabuki, S. et al., "Electro–conductive Enzyme Membrane," *J. Chem. Soc. Commun*, 945–946 (1989).

Yang, L. et al., "Determination of Oxidase Enzyme Substrates Using Cross–Flow Thin–Layer Amperometry," *Electroanalysis*, 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society*, 12(2):487–489 (Nov. 1–4, 1990).

Yao, T. et al., "A Chemically–Modified Enzyme Membrane Electrode As An Amperometric Glucose Sensor," *Analytica Chimica Acta.*, 148:27–33 (1983).

Ye, L. et al., "High Current Density "Wired" Quinoprotein Glucose Dehydrogenase Electrode," *Anal. Chem.*, 65(3):238–241 (Feb. 1, 1993).

Yildiz, A. et al., "Evaluation of an Improved Thin–Layer Electrode," *Analytical Chemistry*, 40(70):1018–1024 (Jun. 1968).

Zamzow, K. et al., New Wearable Continuous Blood Glucose Monitor (BGM) and Artificial Pancreas (AP), *Diabetes*, 39:5A(20) (May 1990).

Zhang, Y. et al., "Application of cell culture toxicity tests to the development of implantable biosensors," *Biosensors & Bioelectronics*, 6:653–661 (1991).

Zhang, Y. et al., "Elimination of the Acetaminophen Interference in an Implantable Glucose Sensor," *Anal. Chem.* 66:1183–1188 (1994).

SUBCUTANEOUS GLUCOSE ELECTRODE

This application is a Continuation of application Ser. No. 09/356,102, filed Jul. 16, 1999, which is a Continuation of application Ser. No. 08/767,110, filed Dec. 4, 1996, which is a Continuation of application Ser. No. 08/299,526, filed Sep. 1, 1994, now U.S. Pat. No. 5,593,852, which application(s) are incorporated herein by reference.

This is a continuation in part of copending U.S. patent application Ser. No. 08/161,682, filed Dec. 2, 1993 now U.S. Pat. No. 5,356,786, which is hereby incorporated by reference for all purposes.

This work was supported in part by the National Institutes of Health (DK42015). Accordingly, the U.S. government may have rights in this invention.

FIELD OF THE INVENTION

The present invention relates to in vivo enzyme biosensors and more specifically to miniature glucose sensors for subcutaneous measurement of glucose with one-point calibration.

BACKGROUND

In response to the need for frequent or continuous in vivo monitoring of glucose in diabetics, particularly in brittle diabetes, a range of possible in vivo glucose electrodes have been studied. The desired characteristics of these electrodes include safety, clinical accuracy and reliability, feasibility of in vivo recalibration, stability for at least one hospital shift of eight hours, small size, ease of insertion and removal, and a sufficiently fast response to allow timely intervention. The in vivo recalibration should be based upon withdrawal of a single sample of body fluid, e.g., blood, and measuring its glucose concentration. This is termed "one point calibration".

Keys to safety are absence of leachable components, biocompatibility, and limiting of the potentially hazardous foreign matter introduced into the body to an amount that is inconsequential in a worst case failure. The clinical accuracy must be such that even when the readings are least accurate, the clinical decisions based on these be still correct. Feasibility of prompt confirmation of proper functioning of the sensors and of periodic in vivo recalibration is of essence if a physician is to allow the treatment of a patient to depend on the readings of the sensor. This one-point calibration, relying on the signal at zero glucose concentration being zero and measuring the blood glucose concentration at one point in time, along with the signal, is of essence, but has heretofore been elusive. The sensitivity must be sufficiently stable for the frequency of required In vivo recalibration to not be excessive. The sensor must be small enough to be introduced and removed with minimal discomfort to the patient and for minimal tissue damage. It is preferred that the sensor be subcutaneous and that it be inserted and removed by the patient or by staff in a physician's office. Finally, its response time must be fast enough so that corrective measures, when needed, can be timely.

In response to some of these needs, needle type and other subcutaneous amperometric sensors were considered. The majority of these utilized platinum-iridium, or platinum black to electrooxidize $H_2O_2$ generated by the glucose oxidase (GOX) catalyzed reaction of glucose and oxygen. In these sensors, the GOX was usually in large excess and immobilized, often by crosslinking with albumin and glutaraldehyde. To exclude electrooxidizable interferants, membranes of cellulose acetate and sulfonated polymers including Nafion™ were used. Particular attention was paid to the exclusion of the most common electrooxidizable interferants: ascorbate, urate and acetaminophen. Also to cope with the interferants, two-electrode differential measurements were used, one electrode being sensitive to glucose and electrooxidizable interferants and the other only to interferants. One strategy for overcoming the problem of interferants, applicable also to the present invention, involves their preoxidation. Another strategy involves shifting, through chemical changes, the redox potential of the polymer in the sensing layer to more reducing potentials. When the redox potential of the polymer is in the region between about −0.15 V and +0.15 V versus the standard calomel electrode (SCE), and the electrodes are poised in their in vivo operation between about −0.10 and +0.25 V, the rate of electrooxidation of interferants such as ascorbate, urate, and acetaminophen is very slow relative to that of glucose through its physiological concentration range. Thus, also the currents from electrooxidation of interferants are small relative to those of glucose.

To make the electrodes more biocompatible, hydrophilic polyurethanes, poly(vinyl alcohol) and polyHEMA membranes have been used.

Several researchers tested GOX-based glucose sensors in vivo and obtained acceptable results in rats, rabbits, dogs, pigs, sheep and humans. These studies validated the subcutaneous tissue as an acceptable glucose sensing site. Good correlation was observed between intravascular and subcutaneous glucose concentrations. They also demonstrated the need for in vivo sensor calibration. Another approach to in viva glucose monitoring was based on coupling subcutaneous microdialysis with electrochemical detection. To control and adjust the linear response range, electrodes have been made glucose-diffusion limited, usually through glucose transport limiting membranes.

Diffusional mediators, through which the $O_2$ partial pressure dependence of the signals is reduced, are leached from sensors. Such leaching introduces an unwanted chemical into the body, and also leads to loss in sensitivity, particularly in small sensors. In microsensors, in which outward diffusion of the mediator is radial, the decline in sensitivity is rapid. This problem has been overcome in "wired" enzyme electrodes, i.e., electrodes made by connecting enzymes to electrodes through crosslinked electron-conducting redox hydrogels ("wires"). Glucose oxidase has been "wired" with polyelectrolytes having electron relaying $[Os(bpy)_2Cl]^{+/2+}$ redox centers in their backbones. Hydrogels were formed upon crosslinking the enzyme and its wire on electrodes. These electrodes had high current densities and operated at a potential of 0.3 V vs. SCE. The electrooxidizable interferants are eliminated through peroxidase-catalyzed preoxidation in a second, nonwired, hydrogen peroxide generating layer on the "wired" enzyme electrode.

SUMMARY OF THE INVENTION

A small (e.g., 0.29 mm), recessed, non-corroding metal (e.g., gold, platinum, palladium) or carbon wire electrode for subcutaneous in vivo glucose monitoring, approaching in its performance all of the above listed requirements, including in vivo one-point calibration, has been produced. The electrode was constructed by depositing active polymer layers into a recess formed by etching away gold from an insulated gold wire.

The active polymer layers, including a sensing layer, a glucose flux-limiting layer, a biocompatable layer, and optionally a peroxidase-based interferant eliminating layer, were protected within the recess against mechanical damage. (The peroxidase-based interferant eliminating layer is not required when a lower redox potential polymer is used, as described above.) The recess and its polymer layers also reduced the transport of glucose to the wire electrode contacting sensing layer.

By limiting the glucose flux, the desired linear response range, spanning the clinically relevant glucose concentration range was obtained. The inventive biosensors are able to accurately measure, for example, approximately 2–30 m$\mu$ glucose and approximately 0.5–10 m$\mu$ lactate, in vivo. The sensor has no leachable components, and its four crosslinked polymer layers contain only about 5 $\mu$g of immobilized material, and only a few nanograms of polymer-bound osmium. Preoxidation of the interferants in one of the four layers makes possible one-point in vivo calibration of the sensor.

DETAILED DESCRIPTION OF THE INVENTION

Figure 1:
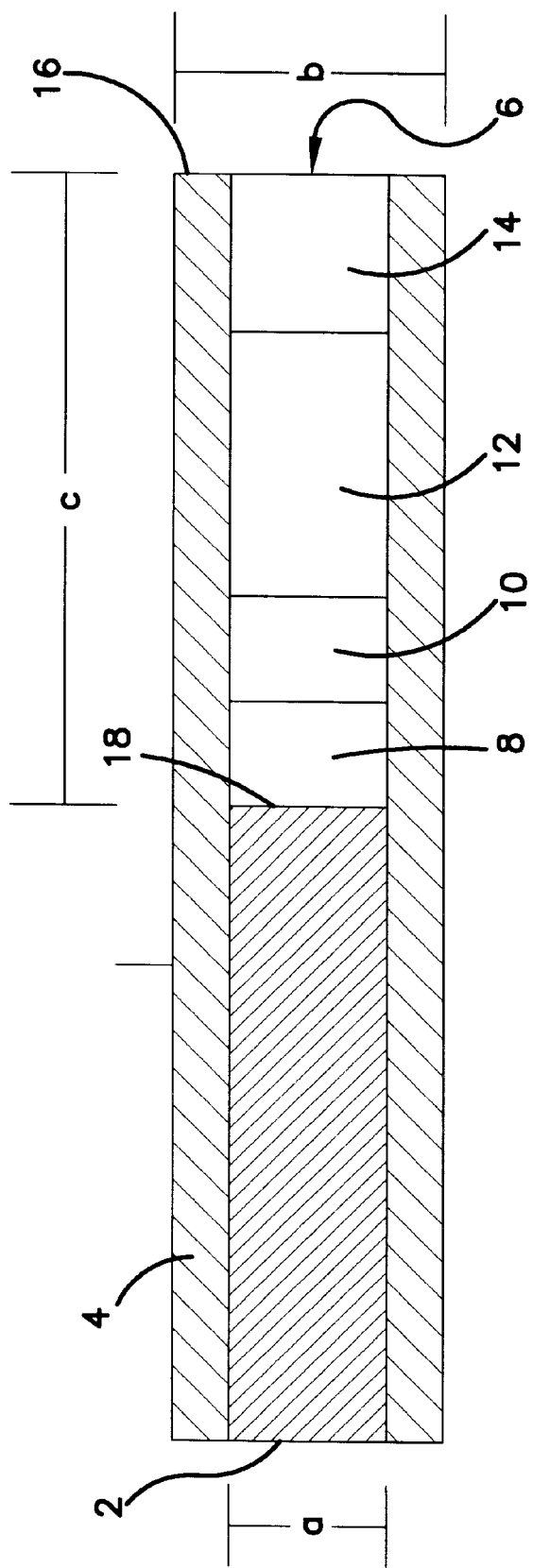
FIG. 1 is a schematic drawing of an electrode of the present invention.

The present invention includes an insulated, non-corroding conducting metal (e.g., gold, platinum, palladium) or carbon wire-based small (e.g., 290 $\mu$m) O.D. subcutaneous glucose sensor, allowing one-point calibration in vivo. As shown in FIG. 1, its construction involves coating a small (e.g., 250 $\mu$m) diameter non-corroding metal or carbon wire 2 with an electrically insulating material 4, e.g., a polyimide, and, layering in a recess 6 formed by etching or removing a portion of the metal or carbon, the following active polymeric layers: an immobilized, "wired," glucose oxidase layer 8; an electrically insulating and glucose diffusion limiting layer 10 formed, for example, by crosslinking a polyallylamine (PAL) with a polyaziridine (PAZ); optionally, an interference eliminating layer 12, e.g., of crosslinked horseradish-peroxidase and lactate oxidase; and a biocompatible film 14 e.g., of poly(ethylene oxide) (PEO) derivatized to allow its photo-crosslinking. The outside diameter a of the wire 2 is preferably about 0.25 mm or less, and the outside diameter b of the insulated wire is preferably about 0.3 mm or less. The recess 6 in the insulated electrode extends from the tip 16 of the electrode which is open to the surrounding environment, to the top 18 of the wire 2 in the insulating sheath, generally for a length c of less than about 0.150 mm, and preferably about 0.125 mm.

The electrodes have no leachable components. The total amount of polymers and enzymes is preferably about 5 $\mu$g. The glucose response through the physiologically relevant 2–20 mM concentration range is close to linear. The electrodes do not respond to ascorbate, urate or acetaminophenol for at least about 36 hours. Their 10–90% response time is about 90 seconds at 2 mM glucose and about 30 seconds at 20 mM glucose. Their sensitivity, after about 30 minutes equilibration, is stable for about 72 hours at 37° C. in 10 mM glucose, the current deviating from the average by less than ±5%. The electrodes have substantially no signal output, e.g., current, charge, or potential, when the concentration of the analyte to be measured is zero.

Two electrodes implanted subcutaneously in a rat tracked blood glucose levels, and their absolute, uncorrected current output was proportional to the blood glucose concentration. Analysis of the correlation between the blood glucose levels in the tail vein and the current output of the sensors in the subcutaneous regions of the thorax and between the scapulae of the same rat showed that even when the probed sites and organs differed in the extreme, one point in vivo calibration was valid. The analysis also showed the value of implanting redundant sensors. Had clinical decisions been made based on individual sensor readings, calibrated at one point, 94% would have been clinically correct. By using redundant sensors and accepting only those pairs of readings that were within one standard deviation, the percentage of the clinically correct decisions was increased to 99%.

It is understood that one of skill in the art may substitute various components of the biosensor described above with known materials to obtain an modified biosensor using the principles outlined herein. For example, the following substitutions are contemplated:

Base electrode: The base electrode of the inventive sensor may be formed of a non-corroding metal or carbon wire, for example vitreous carbon, graphite, platinum, palladium, or gold. Gold is preferred, and is used in the following illustrative examples of the invention.

Insulator: The conductive metal or carbon wire is coated with an electrically insulating material, which also forms a wall about the recess which houses the active polymeric components. The insulating material may be, for example, polyurethane, teflon (fluorinated polymers), polyethylene-terephthalate (PET, Dacron) or polyimide. The insulating material is preferably a biocompatible polymer containing less than about 5% water when in equilibrium with physiological body fluids, e.g., subcutaneous tissue.

Recess: In general, the recess at the tip of the electrode is approximately 20 to 150 μm in length c, and preferably is approximately 50 to 125 μm.

Etching method: The method for etching metal from the tip of the electrode described herein may utilize chloride, bromide or iodide in the bath in lieu of cyanide as described. Bromide is preferred, because it is lose toxic and, like $Au(CN)_2^-$, $AuBr_4^-$ is a water soluble anion. Thus, in aqueous HBR, the metal, e.g., gold, an be etched by applying a sufficiently oxidizing potential where gold is electrolytically dissolved:

Au+4 HBr→$HAuBr_4$+3/2 $H_2$

Wired Enzyme Layer: In the sensing enzyme-containing layer, glucose oxidase may be substituted with other redox enzymes to measure other relevant clinical compounds. For example, lactate oxidase may be used for the in vivo detection of lactate, important in determining if an organ is receiving sufficient oxygen through the blood.

Useful redox polymers and methods for producing the sensing layer are described, for example, in U.S. Pat. Nos. 5,264,104; 5,356,786; 5,262,035, and 5,320,725. Additional redox polymers include, for example, poly(1-vinyl imidazole); poly(4-vinyl pyridine); or copolymers of 1-vinyl imidazole such as poly (acrylamide co-1-vinyl imidazole) where the imidazole or pyridine complexes with [Os $(bpy)_2$ $Cl]^{+/2+}$; [Os (4,4'-dimethyl bipyridine)$_2$Cl]$^{+/2+}$; [Os (4,4'-dimethyl phenanthroline)$_2$Cl]$^{+/2+}$; [Os (4,4'-cimethyoxy phenanthroline)$_2$Cl]$^{+/2+}$; and [Os (4,4'-dimethoxy bipyridine)$_2$Cl]$^{+/2+}$; to imidazole rings. The imidazole ring compounds are preferred because their complexes have more reducing redox potentials, i.e., closer to that of the SCE potential. At these more reducing potentials, the rate of electrooxidation of interferants and the current generated thereby.

Barrier Layer: The polymeric barrier layer is electrically insulating and limits diffusion of glucose through to the sensing layer. It may be formed, for example, by crosslinking a polyallylamine (PAL) with a polyaziridine (PAZ). Alternatively, PAL may be replaced wholly or in part with a zwitterionic polymer obtained by quaternizing poly (vinylpyridine) with bromoacetate and dialyzing against 0.15 M NaCl or by a polyanion such as a polysulfonic acid.

The barrier layer may contain a polyanionic polymer, in which the rate of permeation of anionic interferants such as ascorbate and urate is slowed. This layer may also contain a polycation that enhances the retention of the polyanion by electrostatic bonds and improves wetting by the biocompatable layer.

Interference Eliminating Layer: As described above, this layer is optional, in that it is not required when a redox polymer having a more reducing potential is used, such as $PVI_{15}$-dmeOs (Ohara et al., *Analytical Chemistry*, 1994, 64:2451–2457). At operating potentials of approximately −0.10 to +0.25 for the glucose biosensor, the rate of electrooxidation of interferants such as ascorbate, urate and acetaminophen is very slow relative to that of glucose through its physiological concentration range.

When a separate interferant eliminating layer is used, it preferably contains a peroxidase enzyme which may or may not be preactivated. Such interferant eliminating layers are disclosed, for example, in U.S. Pat. No. 5,356,786 which discloses the structure and function of interferant eliminating biosensors. The glucose biosensor preferably contains lactate oxidase (LOX) in combination with peroxidase in the interferant eliminating layer. However, for biosensors used to detect lactate, glucose oxidase would be used with peroxidase. In a similar manner, the enzyme composition of the interferant eliminating layer may be altered for a specified function.

Biocompatable Layer: In general, the biocompatible layer is comprised of hydrogels, e.g., polymeric compositions which contain more than about 20% by weight of water when in equilibrium with a physiological environment such as living tissue or blood. An example is crosslinked poly (ethylene oxide), e.g., poly(ethylene oxide) tetraacrylate. The polymeric compositions must be non-toxic and compatible with living systems.

Method for making multi-layered recessed biosensors: Insulated non-corroding metal or carbon wires that have been etched as described above to contain a recess at the tip, are placed in a block that serves as an X-Y positioner. The wires vertically traverse the block and are held in place, e.g., by pressure. The blocks with the wires can be formed of elements, each element having multiple half-cylinder grooves running vertically. The wires are placed in these grooves and the elements are assembled into the block using screws. For example, the block may be formed of aluminum having equally spaced holes, (900 for a 30×30 array of wires), each hole to contain one wire. The block is positioned under a fixed micronozzle that ejects a fluid in to the recess of the insulated wire.

To reduce the requirement of precision in the positioning of the block and the micronozzle, the nozzle is electrically charged, with the wire having an opposite charge, or the wire being grounded or at least having a potential such that there is a potential difference between the nozzle and the wire. Because the nozzle is charged, the microdroplets it ejects are also charged with the same type of charge (positive or negative) as the nozzle. The higher the potential on the nozzle (e.g., versus ground potential), the higher the charge on the ejected microdroplets. If the tip of the wire to be coated is at ground potential or has a charge of the opposite type, the charged microdroplets are guided into the recess to deposit on the electrode, even if the jet of microdroplets is not vertical, i.e., even if the micronozzle is not precisely aligned above the wire's tip.

Furthermore, the higher the electrical potential on the nozzle (relative to ground) the greater the charge on the ejected microdroplet. When the charge is high enough, the droplet breaks up into two or more smaller droplets because of electrostatic repulsion of charges on the droplet. Thus, the very small droplets all "drift" (drift meaning transport assisted by an electrical field) to the recessed electrode surface and are collected on it, even if they did not originate in a nozzle precisely aligned with the electrode.

This coating method is useful in making any small biosensor, not only those in recessed zones.

Clinical Use of the Recessed Biosensors: The recessed biosensors of the present invention have sufficient sensitivity and stability to be used as very small, subcutaneous biosensors for the measurement of clinically relevant compounds such as glucose and lactate. The electrodes accurately measure glucose in the range of about 2–30 μM and lactate in the range of about 0.5–10 mM. One function of the implanted biosensor is to sound an alarm when, for example, a patient's glucose concentration is too low or too high. When pairs of implanted electrodes are used, there are three situations in which an alarm is triggered: low glucose concentration, high glucose concentration; sensor malfunction as determined by a discrepancy between paired readings of the two sensors. A discrepancy sufficient to trigger the alarm may be, for example more than two or three times the standard deviation persisting for a defined period, e.g., not less than ten minutes. Such a system may be useful in sleeping patients, and also in emergency and intensive care hospital rooms, where vital functions are continuously monitored.

Another function of the inventive biosensors in to assist diabetics in maintaining their blood glucose levels near normal. Many diabetics now maintain higher than normal blood glucose levels because of danger of coma and death in severe hypoglycemia. However, maintaining blood glucose levels substantially, e.g., approximately 40% or more above normal leads to retinopathy and blindness as well as to kidney failure. Use of the subcutaneous biosensors to frequently, if not continuously, monitor glucose concentrations is desirable so that glucose concentrations can be maintained closer to an optimum level.

The subcutaneous biosensors can be used to measure the rate of rise and decline of glucose concentrations after a meal or the administration of glucose (e.g., a glucose tolerance test). The sensors are also useful in feedback loops for automatic or manually controlled maintenance of glucose concentrations within a defined range. For example, when used in conjunction with an insulin pump, a specified amount of insulin is delivered from the pump if the sensor glucose reading is above a set value.

In all of these applications, the ability to promptly confirm that the implanted sensor reading is accurate is essential. Prompt confirmation and rapid recalibration are possible only when one-point calibration is valid. Generally, even if a sensor's response is linear through the relevant concentration range, calibration requires at least two blood or fluid samples, withdrawn from the patient at times when the glucose concentration differs. It usually takes several hours for the glucose concentration to change sufficiently to validate proper functioning by two-point calibration. The ability to confirm and recalibrate using only one point is thus a highly desirable feature of the present invention.

Redundant sensors (e.g., at least two) are preferred in the clinical application of the subcutaneous biosensors. Such redundancy permits signaling of failure of any one sensor by recognition of an increase in the discrepancy between the readings of the sensors at one time point, e.g., more than two standard deviations apart. The redundant sensors may be implanted near each other or at remote sites.

It is preferred that the biosensors be implanted in subcutaneous tissue so as to make the sensor relatively unobtrusive, and at a site where they would not be easily dislodged, e.g., with turning or movement. It is also preferred, when readings are not corrected for temperature (which they generally are) that the sensors be implanted where they are likely to be at body temperature, e.g., near 37° C., and preferably covered by clothing. Convenient sites include the abdomen, inner thigh, arm.

Although we describe here continuous current measurement for assaying glucose, the electrical measurement by which the glucose concentration is monitored can be continuous or pulsed. It can be a current measurement, a potential measurement or a measurement of charge. It can be a steady state measurement, where a current or potential that does not substantially change during the measurement is monitored, or it can be a dynamic measurement, e.g., one in which the rate of current or potential change in a given time period is monitored. These measurements require at least one electrode in addition to the sensing electrode. This second electrode can be placed on the skin or can be implanted, e.g., subcutaneously. When a current is measured it is useful to have a potentiostat in the circuit connecting the implanted sensing electrode and the second electrode, that can be a reference electrode, such as an Ag/AgCl electrode. When a current is measured the reference electrode may serve also as the counter electrode. The counter electrode can also be a separate, third electrode, such as a platinum, carbon, palladium or gold electrode.

In addition to implanting the sending electrode in the body, fluid from the body, particularly fluid from the subcutaneous region, can be routed to an external sensor. it is preferred in this case to implant in the subcutaneous region a microfiltration giver and pull fluid to an evacuated container, the fluid traversing a cell containing the sensing electrode. Preferably this cell also contains a second electrode, e.g., a reference electrode which may serve also as a counter electrode. Alternatively, the reference and counter electrodes may be separate electrodes. In coulometric measurements only two electrodes, the sensing electrode and the counter electrode are required. The flow of body fluid amy be pulsed or continuous. Other than an implanted microfiltration fiber, also a microdialysis fiber may be used, preferably in conjunction with a pump.

Increased stability of the biosensors: To increase the stability and useful life of the inventive biosensors, it is advantageous to use intrinsically more stable enzymes and redox polymers. However, even if the enzyme and redox polymer degrade in the glucose electrooxidation process by which the signal (current) is generated, it is possible to greatly extend the useful life of the implanted electrodes and reduce the frequency of their required recalibration after implantation.

A simple measure by which the life of the implanted electrodes can be extended and the frequency of their required recalibration reduced involves turning the electrodes "on" by applying a bias, i.e., a potential, only during the period of measurement, then turning the biasing potential off or reducing it, so that a lesser current will flow. It is generally sufficient to perform only one measurement every five or even ten minutes, or longer, because glucose concentrations do not change abruptly.

Another measure is to lower the glucose flux to the sensing layer much as possible, consistent with maintaining adequate sensitivity and detectivity. Reduction of the glucose flux to the sensing layer reduces the current. Therefore, even though this stabilizes the electrodes, i.e., slows the loss in sensitivity, the flux dependent current must not be excessively reduced. Usually a current of 3–5 nA at 2 mM glucose concentration is adequate. When the glucose flux is lowered by using one or more glucose-flux reducing polymer slayers, such as the PAL/PAZ layer, the lifetime of the sensor is increased.

EXAMPLE

Example 1

Electrode Preparation

Electrodes were made of a polyamide-insulated 250 $\mu$m diameter gold wire, having an outer diameter (O.D.) of 290 $\mu$m (California Fine Wire Co., Grover City, Calif.). Heat shrinkable tubing (RNF 100 3/64" BK and 1/16" BK, Thermofit™, Raychem, Menlo Park, Calif.) and a two component silver epoxy (Epo-tek $H_2OE$; Epoxy Tech, Inc., Billerica, Mass.) were used for electrode preparation.

The glucose sensing layer was made by crosslinking a genetically engineered glucose oxidase (rGOX) (35% purity, Chiron Corp., Emeryville, Calif.) with a polymer derived of poly(vinylimidazole) (PVI), made by complexing part of the imidazoles to $[Os(bpy)_2Cl]^{+/2+}$. The resulting redox polymer, termed PVI-Os, was synthesized according to a previously published protocol. (Ohara et al., 1993, Anal. Chem., 65:24). Poly(ethylene glycol) diglycidyl ether 400 (PEDGE; Polysciences, Warrington, Pa.) was used as the crosslinker.

The barrier layer between the sensing and interference-eliminating layers was made of polyallylamine (PAL; Polysciences) crosslinked with a polyfunctional aziridine (PAZ) (XAMA-7; Virginia Chemicals, Portsmouth, Va.).

The interference-eliminating layer was prepared by co-immobilizing horseradish peroxidase (HRP) type VI (Cat. no. P-8375, 310 U/mg, denoted herein as HRP-VI, Sigma, St. Louis, Mo.) and HRP for immunological assay (No. 814407, min 1000 U/mg, denoted HRP-BM, Boehringer-Mannheim, Indianapolis, Ind.) with lactate oxidase from Pediococcus sp. (Cat. No. 1361, 40 U/mg denoted LOX, Genzyme, Cambridge, Mass.) and a recombinant microbial source (Cat. No. 1381 denoted rLOX, Genzyme). Co-immobilization was performed using sodium periodate (Cat. No. S-1147, Sigma) according to the methods described in Maidan and Heller, 1992, Anal. Chem. 64:2889–2896.

The biocompatible layer was made of 10% aqueous poly(ethylene oxide) tetraacrylate (PEO-TA). To form the photocrosslinkable polymer, PEO was acrylated by reaction with acryloyl chloride. The 18,500 g/mol PEO (Polysciences) is a tetrahydroxylated compound by virtue of two hydroxyl groups on a bisphenol A bisepoxide that linked two a, ω-hydroxy-terminated 9,000 g/mol PEO units. Acryloyl chloride (Aldrich, Milwaukee, Wis.) in a 2 to 5 molar excess was used to acrylate the polymer (10% w/v PEO in benzene). Triethylamine (Mallinkrodt, Paris, Ky.) was used as a proton acceptor equimolar with theacryloyl chloride.

Other chemicals used were bovine serum albumin (BSA) fraction V (Cat. No. A-2153), BSA, ascorbic acid, uric acid, 4-acetaminophenol, L(+)=lactic acid, and hydrogen peroxide 30%, all from Sigma. All chemicals were used as received. Solutions (if not otherwise specified) were made with distilled, deionized water. Glucose monitoring was performed in buffer, in bovine serum (Sigma, Cat. No. S-6648) containing antibiotic-antimycotic solution (Sigma, Cat. No. A-8909) at 37° C. and in rats.

Instrumentation

In making the recessed gold electrodes, a potentiostat/galvanostat (PAR Model 173, Princeton Applied Research, Princeton, N.J.) operated in a galvanostatic mode, and a sonicator (Fisher Scientific, Pittsburgh, Pa.) were used. Cyclic voltammograms were recorded with a potentiostat (PAR Model 273A) and a conventional electrochemical cell having a Pt wire counter and a SCE reference electrode and were evaluated with PAR 270 software. Glucose signals were monitored with a bipotentiostat (Biometra EP 30) and a two channel strip-chart recorder. The recessed electrodes were coated under a microscope (Bausch & Lomb) using a micromanipulator (Narishige, Seacliff, N.Y.). The micropipettes were pulled with a micropipette puller (Narishige). Temperature was controlled with an isothermal circulator (Fisher Scientific).

Electrode Preparation:

Five cm lengths of polyamide insulated gold wire were cut with a sharp razor blade. Electrical contact was made at one end with silver epoxy to an insulated stainless steel wire and the junction was covered with insulating heat shrinkable tubing. The recess forming electrochemical etching process was carried out in 10 ml of 3 M potassium cyanide, with the gold wire as the working electrode and a platinum or gold wire as the counter electrode. The wires were placed in contact with the bottom of the beaker, all electrodes being equidistant from the counter electrode. The beaker was sonicated during the etching procedure. The ends of the gold wires were bent upwards, so that agitation by the sonicator caused the oxygen bubbles formed during the etching process to rise and escape. The electrodes were then thoroughly washed and immersed in water for 30 minutes.

A recess 6, i.e., channel, in a polyamide insulated gold wire 2 is formed by electrochemical etching of the gold under galvanostatic control. By controlling the charge, the total amount of gold electrooxidized and dissolved as $Au(CN)_2$ is defined. When the conditions were set so that the CN— transport into the channel and the $Au(CN)_2$— transport out of it are not rate limiting, (e.g., sonicated bath and high concentration of potassium cyanide, at least approximately 0.2 M, and preferably 3 M), a flat gold wire surface is produced at the bottom of channels with aspect ratios of 0.5 to 2.0. Thus, when the CN— concentration is high enough and the wires are ultrasonically vibrated, the tips of gold wires are flat. Passage of 1.5 coulombs per electrode at 8 mA current produced approximately 125 μm deep cavities or channels. At theoretical efficiency for one-electron oxidation, 3.08 mg of gold would have been etched. The amount of gold actually etched was only 0.076 mg, showing significant CN— or water oxidation. Nevertheless, the process is reproducible, accurate and fast with 20 electrodes being processed in each batch in less than five minutes. The recess-forming procedure was highly reproducible, with a deviation of ±10 μm found (using an objective micrometer) for a batch of 30 recessed electrodes. Before coating, the electrodes were examined under a microscope for flatness of the gold surface and correct depth.

FIG. 1 shows a schematic side view in cross-section of an electrode of the present invention, showing the gold wire 2, insulating coating 4, and recess or channel 6. The recessed gold surfaces were coated by filling of the cavities or channels 6 with aqueous solutions containing the crosslinkable components of the different layers, and their crosslinkers. The solutions were introduced under a microscope with a micropipette (connected to a microsyringe by polyethylene tubing and shrink tubing), using a micromanipulator. After application of each of the individual layers, the electrodes were cured overnight at room temperature, in air.

Electrode structure:

The electrodes were prepared by sequentially depositing four layers within the recess or channel 6. The layers were: the sensing layer 8, the insulating layer 10, the interference-eliminating layer 12 and the biocompatible layer 14. The sensing layer, containing "wired" redox enzyme is positioned adjacent to and in contact with the gold wire 2. The insulating layer 10 is positioned between the sensing layer 8 and the peroxidase-based interferant-eliminating layer 12. The biocompatible layer 14 fills the remaining space in the recess 6 and is in contact with the environment outside the electrode. The thin polymer layers are well protected by containment within the polyamide sleeve 4.

The sensing layer 8 was made by "wiring" rGOX to the gold electrode through a redox hydrogel to which the enzyme was covalently bound. The electrodes were prepared as follows: 10 mg/ml solutions were made from 1. the PVI-Os redox polymer in water,
2. the crosslinker, PEGDGE, in water, and
3. the enzyme, rGOX, in a 10 mM HEPES solution adjusted to pH 8.15.

A redox hydrogel was formed by mixing the three solutions so that the final composition (by weight) was 52% redox polymer, 35% enzyme and 13% crosslinker.

The insulating layer 10 prevented electrical contact between the redox hydrogel and the interference eliminating enzymes (HRP and LOX). PAL:PAZ was used as the insulating material. The film was deposited from a solution obtained by mixing in volume ratio of 1/1, 1/2 or 1/3, a PAL solution (4.5 mg in 100 mM HEPES buffer at pH 7.0) and a freshly prepared PAZ solution (30 mg/ml). The PAZ solution was used within 15 minutes of preparation.

The interference-eliminating layer 12 was prepared according to a previously published protocol, Maidan and Heller, 1992, *Anal. Chem.*, 64:2889–2896. 50 µl of a 12 mg/ml freshly prepared sodium periodate solution was added to 100 µl of a solution containing 20 mg/ml HRP (HRP-VI or HRP-BM) and 100 mg/ml LOX (LOX or rLOX) in 0.1 M sodium bicarbonate and the mixture was incubated in the dark for two hours. Alternatively, the oxidation of HRP could be carried out prior to adding LOX and crosslinking.

The biocompatible layer 14 films were photocrosslinked by exposure to UV light (UVP, Inc., San Gabriel, Calif.; Blak-Ray; spectral peak at 360 nM, UV irradiance at the sample 200 mW/cm$^2$) for one minute. The initiator used was 2,2-dimethoxy-2-phenylacetphenone (Aldrich). A solution of 300 mg/ml of the initiator in 1-vinyl-2-pyrrolidinone (Aldrich) was added to the prepolymer mixtures. Approximately 30 µl of the initiator solution was added per ml of 10% w/w aqueous solution of the tetraacrylated PEO. The prepolymers were crosslinked in situ inside the recess of the electrode. The films were prepared by filling the recess with the prepolymer solution twice and exposing the electrode to the UV light source after each time the cavity was filled.

In vitro Testing of Electrodes:

In vitro experiments were carried out in batch fashion at 25° and 37° C., using a conventional three electrode electrochemical cell with the enzyme-modified gold wire as the working electrode, a platinum wire as the counter electrode and a saturated calomel reference electrode (SCE). The electrolyte was a 20 mM phosphate buffered-saline solution containing 0.15 M NaCl at pH 7.15. Experiments in serum were performed at 37° C., adding 100 µL antibiotic-antimycotic solution to 10 ml serum. Phosphate buffered-saline and serum were agitated during the experiments. The working potential was +0.3 V versus SCE for experiments with the PVI-Os polymers.

Structure and Performance:

The depth c of the channel 6 and the thickness of the polymer layers in it controls the mass transport, i.e., flux of glucose, to the sensing layer. By controlling these parameters, the apparent Michaelis constant ($K_m$) is adjusted to about 20–30 mM glucose. The polyimide wall 4 of the channel 6 also protects the four polymer and polymer/enzyme layers 8, 10, 12, 14 against mechanical damage and reduces the hazard of their loss in the body. Because the glucose electrooxidation current is limited by glucose mass transport through the recess 16 and its polymer films 8, 10, 12, 14, rather than by mass transport to the tissue-exposed tip 16, the current is practically insensitive to motion. Evidently, the electrooxidation rate of glucose in the recessed sensing layer 8 is slower than the rate of glucose diffusion to the channel's outer fluid contacting interface.

Figure 2:
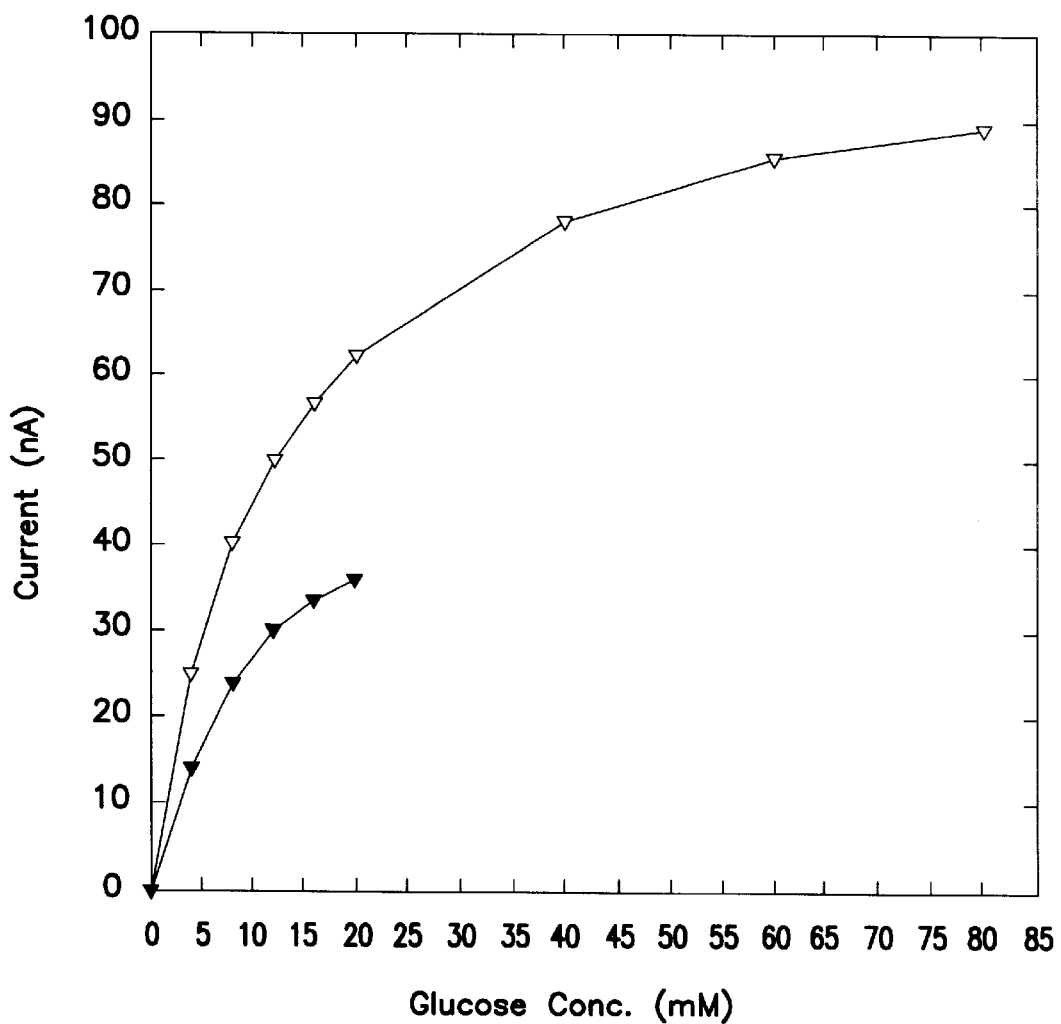
FIG. 2 is a graphical representation of data generated comparing current density of glucose electrooxidation on electrodes made with PVI$_5$-Os (open triangles) with those made with PVI$_3$-Os (filled triangles).

PVI$_5$-Os is preferred as the "wire" of the sensing layer when an interference eliminating layer of HRP and LOX is used, but not in the absence of this layer, i.e., when redox polymers with more reducing redox potential are preferred. The subscript (5) is used to indicate that, on the average, every fifth vinylimidazole mer carries an electron-relaying osmium center. Use of electrodes formed with PVI$_5$-Os and PVI$_3$-Os (every third 1-vinylimidazole mer carrying an osmium center) are compared in FIG. 2, and show higher current density of glucose electrooxidation on electrodes made with PVI$_5$ - Os (open triangle) than on those made with PVI$_3$ - Os (filled triangles).

Figure 3:
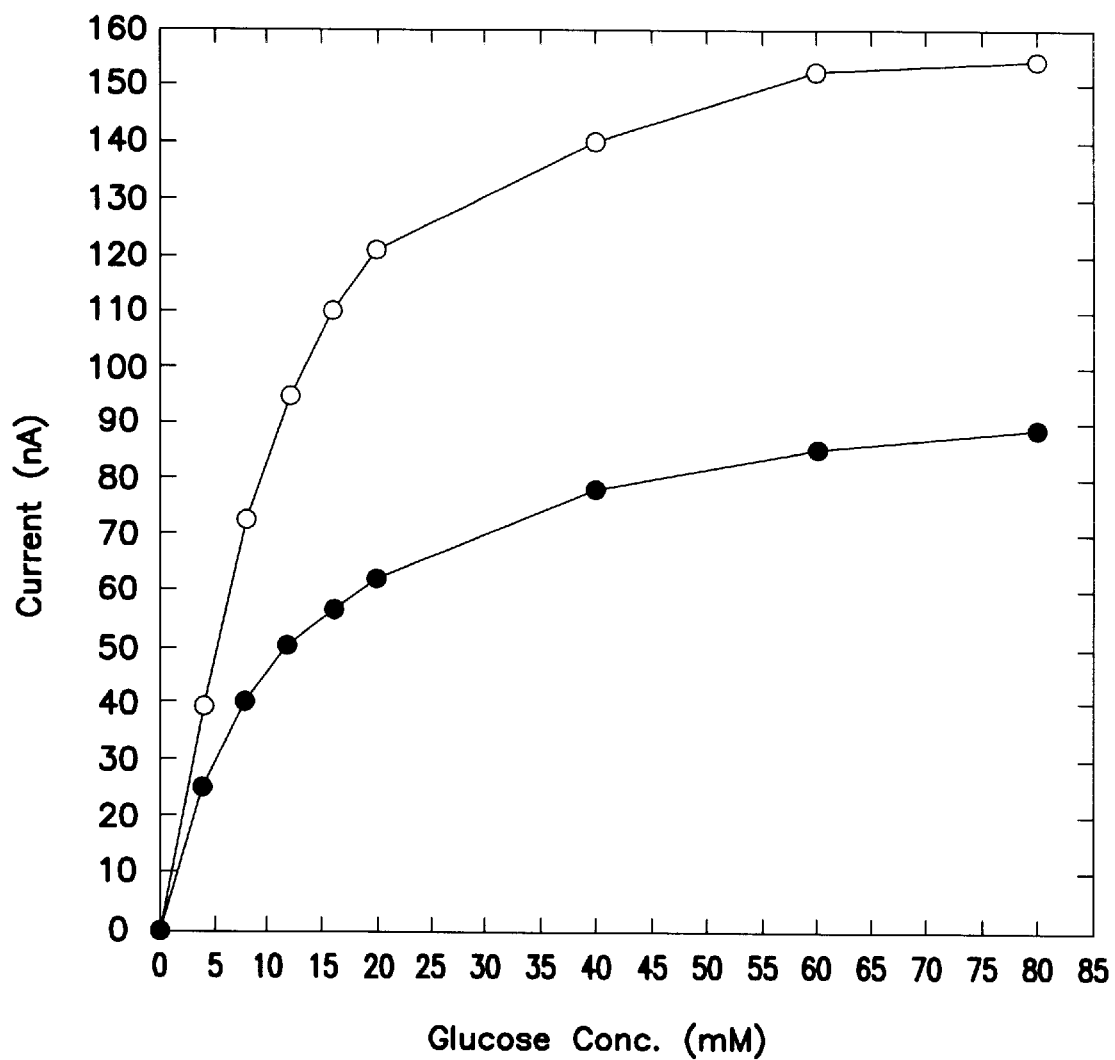
FIG. 3 is a graphical representation of data generated comparing dependency of current generated on the depth of the recess.
Figure 4:
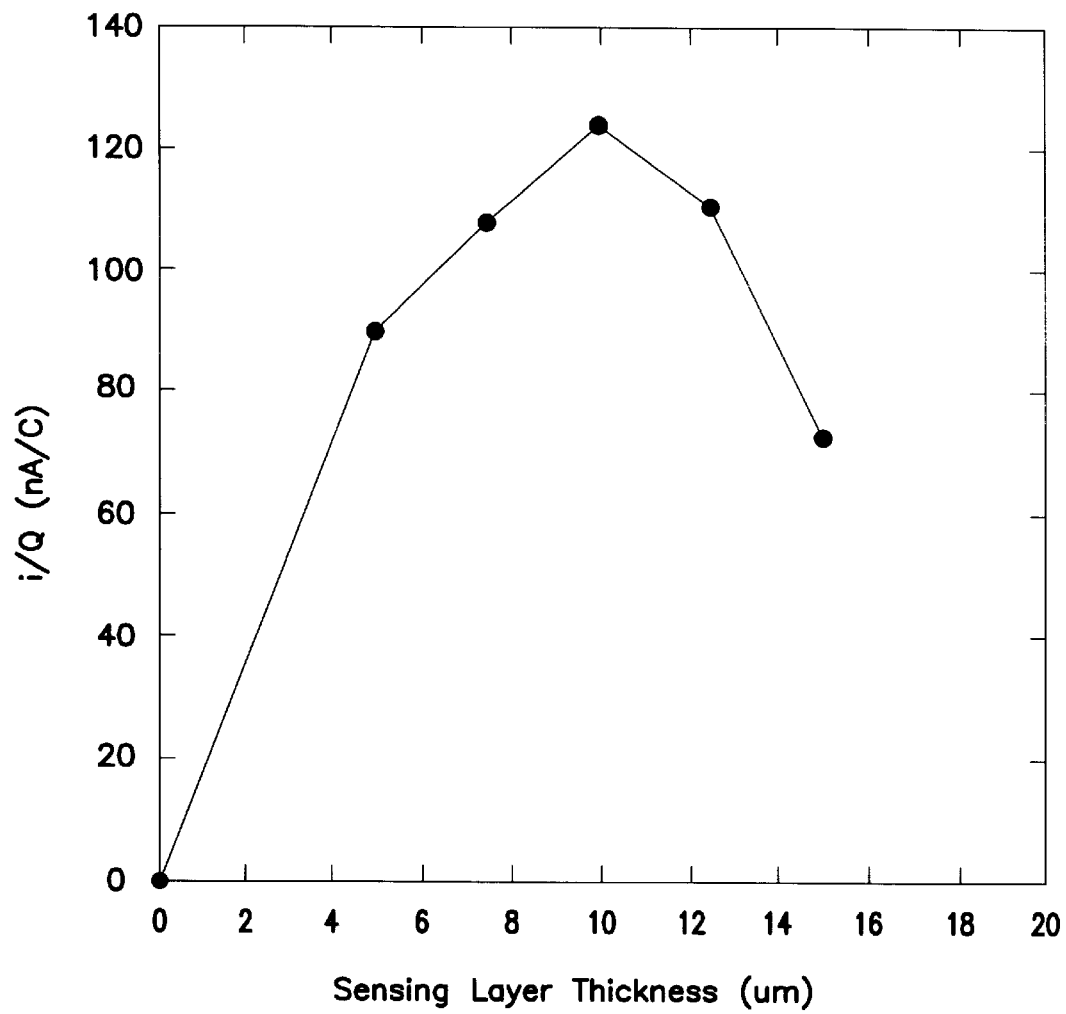
FIG. 4 is a graphical representation of data generated comparing dependency of the ratio of the current generated and the charge required to electoreduce or oxidize the polymer redox centers in the sensing layer on the thickness of the sensing layer.

Depth of the recess and the sensing layer:

Channels of 125, 250, and 500 µm depth, were investigated to assess the dependence of the current on the depth of the recess (FIG. 3), with the total amount of PVI$_5$ - Os and rGOX being kept constant. Much of the loss in current in the deeper cavities resulted not from reduced glucose mass transport, but from adsorptive retention of part of the enzyme and polymer on the polyamide wall when microdrops of the component solutions were introduced into the recess in the process of making the electrodes. Through repeated rinsing with water, some of the adsorbed polymer and enzyme on the walls were washed onto the electrode surface, increasing the current. The highest currents were seen after five washings. When the thickness of the sensing layer was increased through increasing the number of coatings (FIG. 4) the ratio of current to charge required to electroreduce or electrooxidize the redox polymer in the sensing layer reached a maximum, then dropped. For the preferred 125 µm recess, 10 coatings, producing an approximately 13 µm thick wired-rGOX sensing layer, yielded sensors that had the desired characteristics for in vivo use.

The insulating layer:

This layer electrically insulates the redox enzymes of the interference eliminating layer (HRP and LOX) from the "wired" rGOX layer and limits the glucose flux to the sensing layer, thereby extending the useful life of the electrode. PAL crosslinked with PAZ, forming a polycationic network at pH 7.09 is preferred. The best results, i.e., best stability of current outputs, were obtained using 1:2 PAL: PAZ (FIG. 5), with three coatings applied to form an approximately 7 µm thick crosslinked film.

Figure 6:
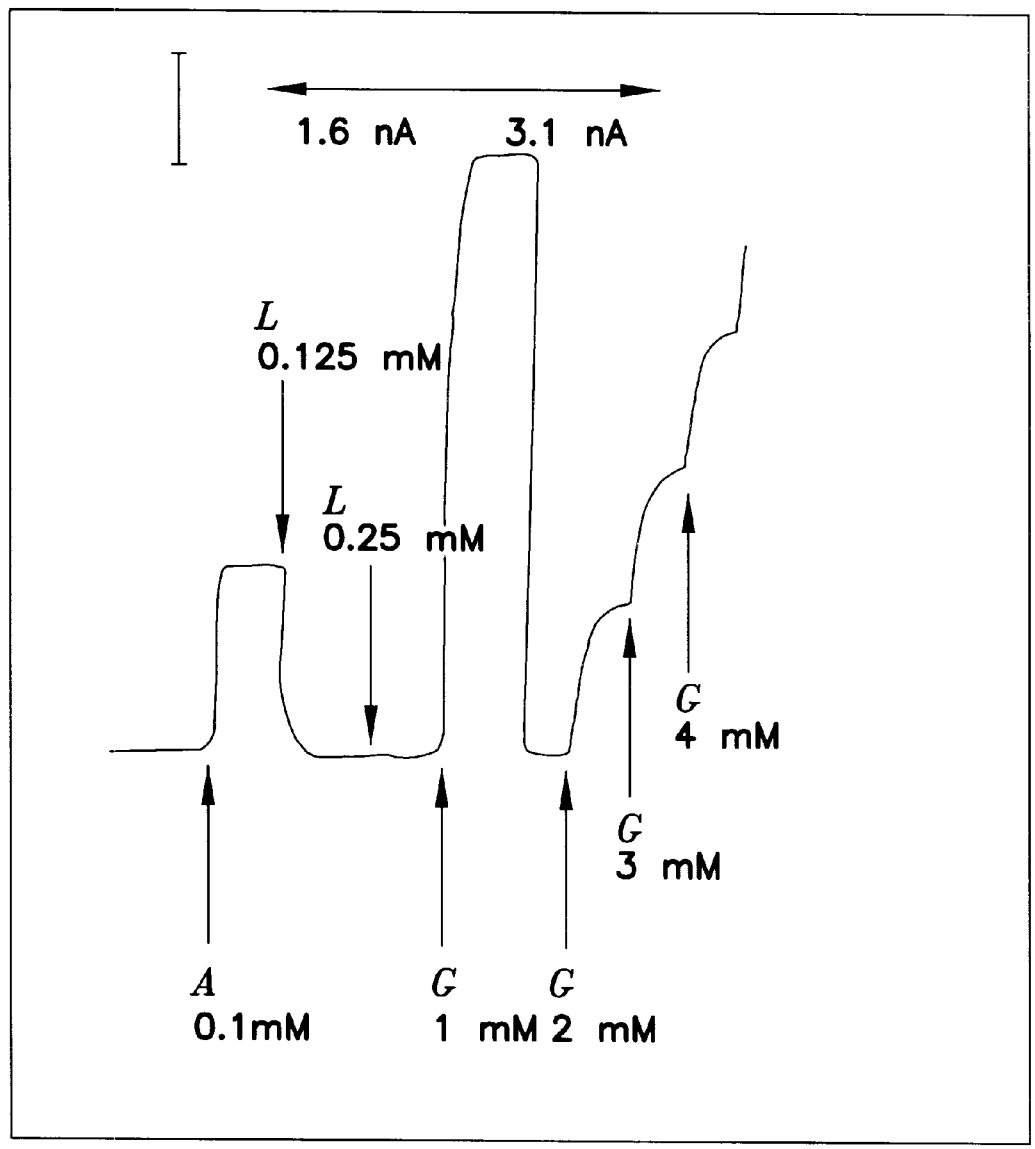
FIG. 6 is a graphical representation of data generated comparing dependency of current generated on the presence of ascorbate, in the absence and presence of lactate and glucose. The concentrations of ascorbate (A), lactate (L) and glucose (G) are shown. Ascorbate is an electrooxidzable interferant. Upon addition of lactate its electrooxidation current is suppressed while that of glucose is not suppressed.

The interference eliminating layer:

Interferants, particularly ascorbate, urate, and acetaminophenol, are oxidized in the third layer, containing LOX and HRP. In this layer, lactate, the typical concentration of which in blood is 1 mM, reacts with $O_2$ to form $H_2O_2$ and pyruvate. $H_2O_2$, in the presence of HRP, oxidizes ascorbate, urate, and acetaminophenol, being reduced to water. The preferred coimmobilization process involved two separate steps: periodate oxidation of oligosaccharide functions of HRP to aldehydes, followed by mixing with LOX and formation of multiple Schiff bases between HRP-aldehydes and LOX amines (e.g. lysines) and between HRP aldehydes and amines. The thickness of the interference eliminating layer is approximately 85 µm and is made by applying successive coatings, e.g., about six coatings. FIG. 6 shows that electrooxidizable interferants were eliminated in the presence of lactate at physiological levels. LOX slowly lost its activity in the crosslinked HRP-LOX layer. This led to degradation of the ability of the layer to eliminate interferants. After 36 hours of operation at 37° C., a measurable current increment was noted when enough ascorbate was added to produce a 0.1 mM concentration.

The biocompatible layer:

A preferred biocompatible layer consists, for example, of photocrosslinked tatraacrylated 18,500 Da poly(ethylene oxide) (Pathak et al., 1993, *J. Am. Chem. Soc.,* 114:8311–8312). The thickness of this layer, made by sequential photo-crosslinking of two coatings, is about 20 μm. One minute UV exposure required for the photo-crosslinking process reduced the sensitivity by 16±2%.

Example 2

In vivo use of sensor

The objective of this experiment was to establish the validity of a one-point in vivo calibration. Two sensors were simultaneously implanted subcutaneously in a rat, one on the thorax, the second between the scapulae. To make the difference between the blood sampled and the subcutaneous fluid proved with the sensors as extreme as possible, i.e., to probe whether the one-point calibration holds even if the organs sampled are different and the sampling sites are remote, blood was withdrawn from the tail vein. Blood glucose levels were periodically measured in withdrawn samples, while the absolute uncorrected sensor current output was continuously monitored.

In vivo experiments (6–10 hours) were carried out in 300 g male Sprague-Dawley rats. The rats were fasted overnight and prior to the experiment were anaesthetized with an intraperitoneal (i.p.) injection of sodium pentobarbital (65 mg/kg rat wt). An i.p. injection of atropine sulfate (166 mg/kg rat wt) was then administered to suppress respiratory depression. Once the rat was anaesthetized, a portion of the rat's abdomen was shaved, coated with a conductive gel, and an Ag/AgCl surface skin reference electrode was attached. This electrode served also as the counter electrode. Sensors were then implanted subcutaneously using a 22 gauge Per-Q-Cath Introducer (Gesco International, San Antonio, Tex.) on the rat's thorax, or subcutaneously in the intrascepular area through a small surgical incision. The sensors were taped to the skin to avoid sensor movement. The sensors, along with the reference electrode, were connected to an in-house built bipotentiostat. The operating potential of the sensors was 0.3 V vs. Ag/AgCl, with the Ag/AgCl electrode serving as both the reference counter electrode. Sensor readings were collected using a data logger (Rustrak Ranger, East Greenwich, R.I.) and at the end of the experiment were transferred to a computer. During the experiment, [] the rat's body temperature was maintained at 37° C. by a homeostatic blanket. The sensors were allowed to reach a basal signal level for at least one hour before blood sampling was started. Blood samples were obtained from the tail vein and all blood samples were analyzed using a glucose analyzer (YSI, Inc., Yellow Springs, Ohio; Model 23A).

Approximately thirty minutes after the start of blood sampling, an i.p. glucose infusion was started using a syringe pump (Harvard Apparatus, South Natick, Mass.) at a rate of 120 mg glucose/min kg rat wt. The glucose infusion was maintained for approximately one hour.

Figure 7:
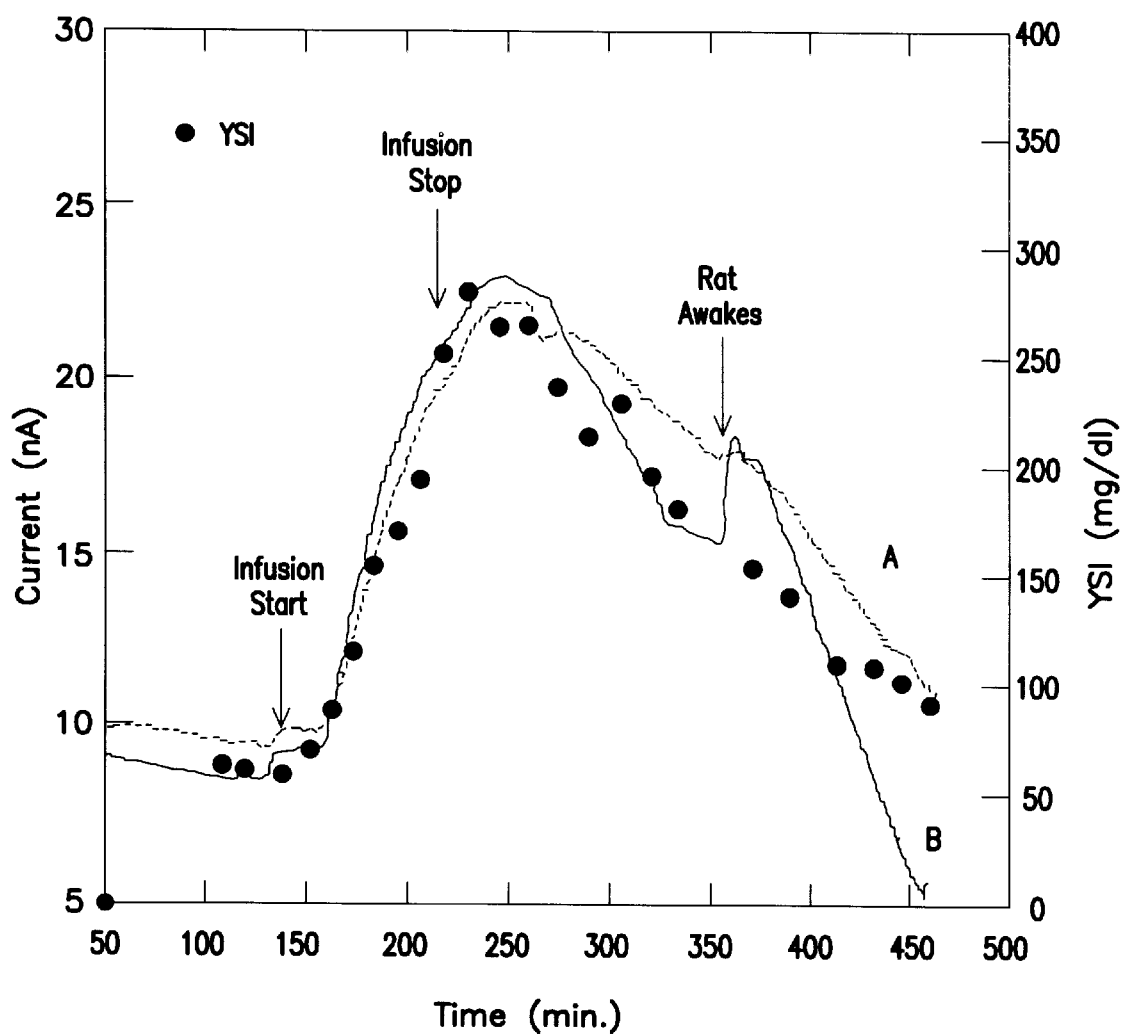
FIG. 7. is a graphical representation of data showing current density and corresponding subcutaneous glucose concentration measured with the subcutaneously implanted electrodes of the present invention in a rat animal model. Large solid circles show blood glucose concentrations measured on withdrawn blood samples using a YSI analyzer.
Figure 8:
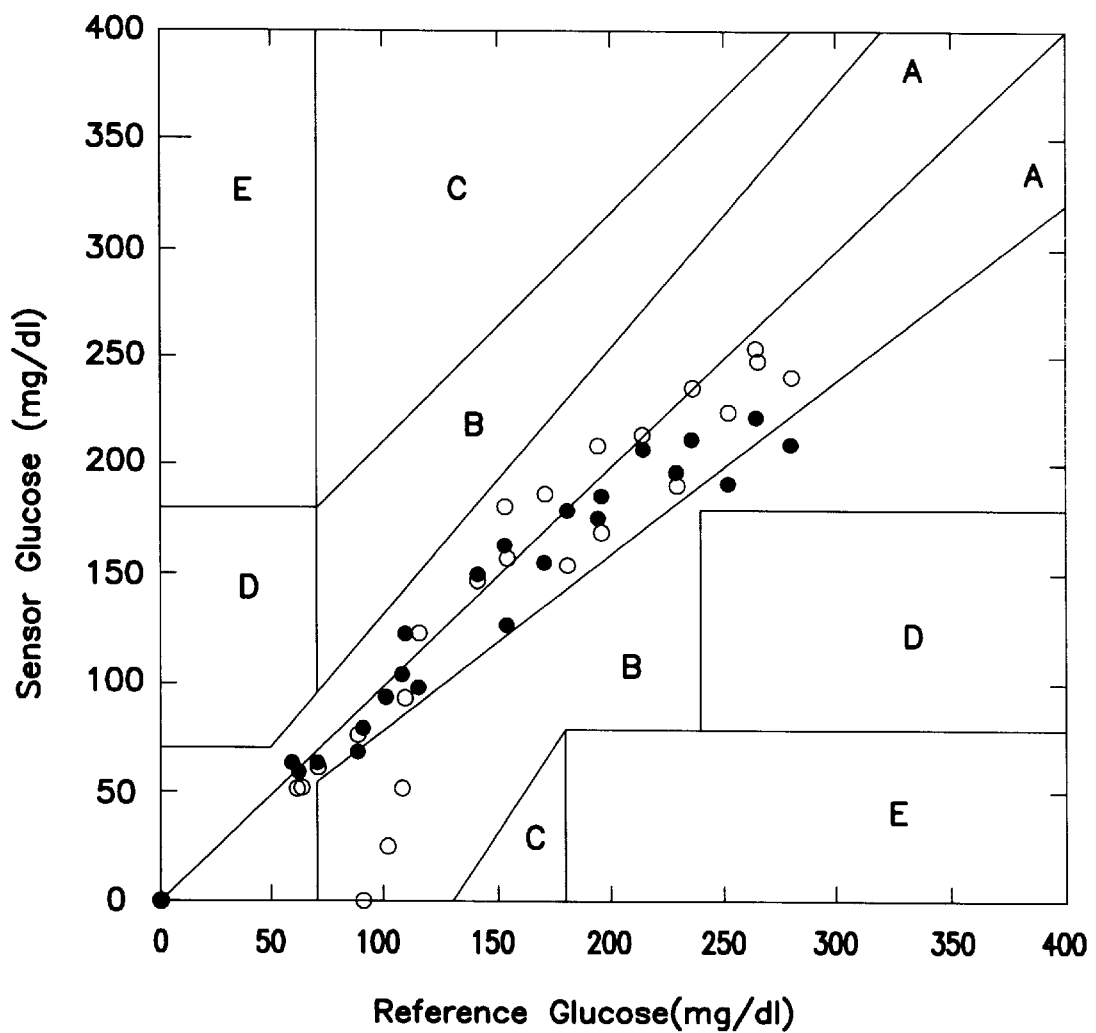
FIG. 8 is a Clarke-type clinical grid analyzing the clinical relevance of the blood glucose measurements of FIG. 7.

As seen in FIG. 7, at 410 min the current dropped precipitously. Such a drop was observed in other measurements with subcutaneously implanted electrodes between 400 and 600 min, but was never observed in electrodes operated in buffer at 37° C. When the failed electrodes were withdrawn and retested in buffer, most of their original sensitivity was found to be intact. The cause for this apparent deactivation was failure of the counter/reference Ag/AgCl electrode on the rat's skin to make good electrolytic contact, and was not due to any failure of the implanted sensor. Using an arbitrarily chosen point to calculate a calibration curve for each electrode, i.e., one blood glucose level determination and one current measurement to establish the scales, all the data from FIG. 7 were plotted in a Clarke-type, (Clarke et al., 1987, *Diabetes Care,* 5:622–627) clinical grid (FIG. 8), without further correction. In this analysis, points falling in region A of the grid are considered clinically accurate, while those in region B are considered clinically correct. Points falling in region C are not correct, but would not lead to improper treatment. Points in regions D and E are incorrect and if treatment would rely on these, it would be improper.

All of the points, from both electrodes, were in regions A and B, with 43 of the 48 points being in region A. The three points in region B near 100 mg/dl glucose, for the electrode implanted between the scapulae, were the last three points of the experiment, at about 410 min. Notwithstanding the failure mode at 400–600 min because of poor electrolytic contact of the counter/reference electrode with the skin and failure after 36 hours by deactivation of the lactate oxidase, resulting in loss of interference elimination, one-point calibration is shown here to be practical. After such calibration, the readings of the subcutaneous sensors provide, without any correction, clinically useful estimates of blood glucose levels.

Figure 9:
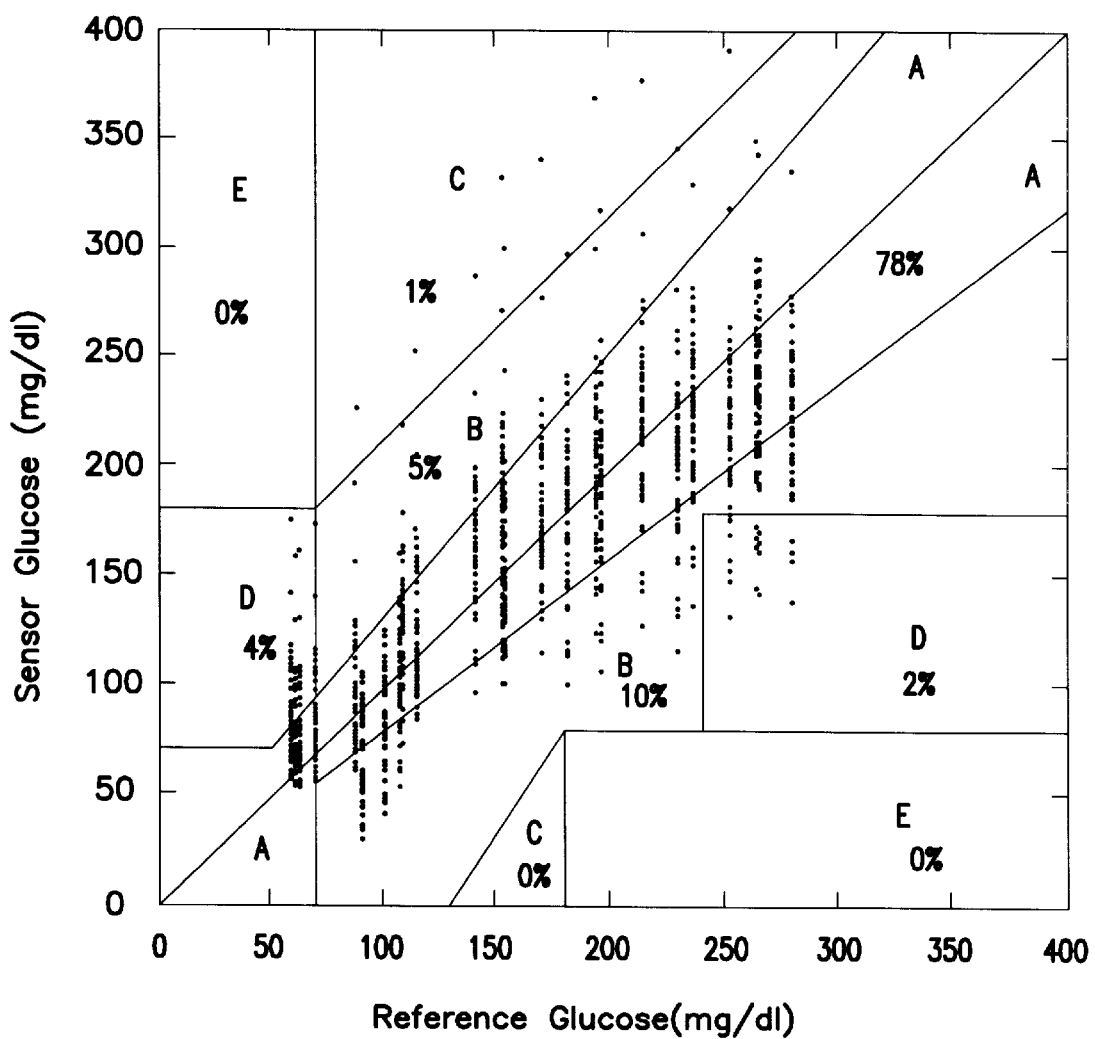
FIG. 9 is a Clarke-type clinical grid of all possible correlations obtained when each of the 24 glucose analyses of FIG. 7 were used for single point calibration of either implanted electrode.

FIG. 9 shows the distribution of all possible correlations obtained when each of the 24 glucose analyses was used for single point calibration of either implanted electrode. There are 2×24×24=1152 points in the distribution. Of these, 78% are in region A, 15% are in region B, 1% in region C, 6% are in region D, and no points are in region E.

Figure 10:
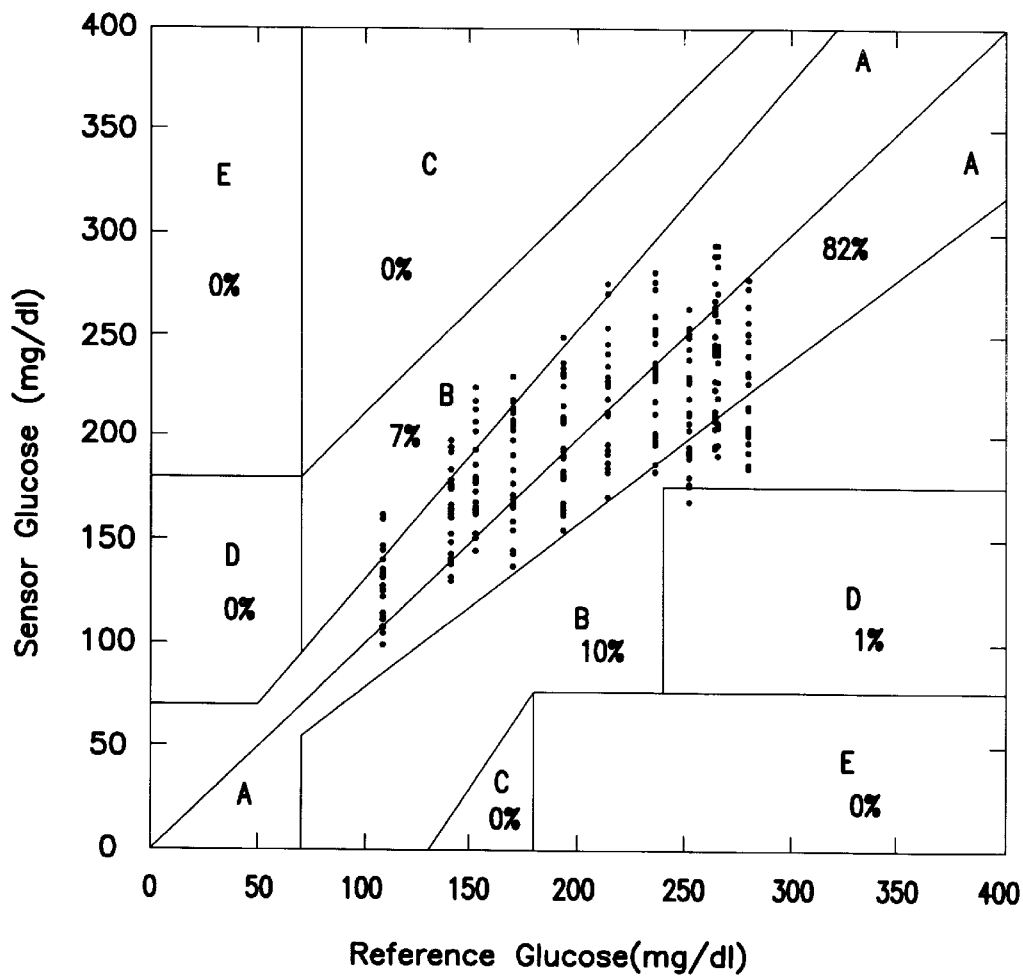
FIG. 10 is a Clarke-type clinical grid testing improvement of the single point calibration through redundant electrodes, the readings of which were within the standard deviation calculated for all differences between simultaneous readings by a pair of implanted electrodes.

In FIG. 10, we tested for the improvement of the single point calibration through using redundant electrodes. First, the readings of electrode A were normalized with respect to those of electrode B by multiplying each reading by the average output of electrode B divided by the average output of electrode A. Next the standard deviation was calculated for the differences between the 24 sets of readings of implanted electrode B and corrected readings of implanted electrode A. Then, all those sets of readings that differed by more than the standard deviation were rejected. The number of sets was reduced thereby from 24 to 11; 82% of the points were in region A, 17% in region B, 1% in region D, and no points in regions C and E. The distribution demonstrates that the sensors can be calibrated through a single independent measurement of the glucose concentration in a withdrawn blood sample. They also demonstrate the improvement in clinical accuracy resulting from the use of redundant subcutaneous sensors. The selection of those data points that differed by less than the standard deviation for the entire set led to a sixfold reduction in the probability of clinically erring in a decision based on readings of the implanted sensors.

Stability and Other Characteristics:

In order to improve the stability, more thermostable recombinant GOX, (rGOX; Heller, 1992, *J. Phys. Chem.,* 96:3579–3587) rather than GOX is used in the sensor and glucose transport is reduced to make the sensor current diffusion, not enzyme turnover, limited. The glucose flux is attenuated by the three outer layers and the sensing layer itself. Because the sensing layer contains a large excess of glucose oxidase, its activity greatly exceeds that needed for electrooxidizing the attenuated glucose flux, and the sensor's stability is improved.

The stability can be tested by methods known, for example, tested in the presence of 0.1 mM ascorbate in 10 mM glucose at 37° C. The current output of a typical optimized electrode was about 35 nA and the apparent $K_m$, derived from an Eadie-Hofstee plot, was about 20 mM (Table 1). The 10–90% response time was approximately one minute.

Figure 5:
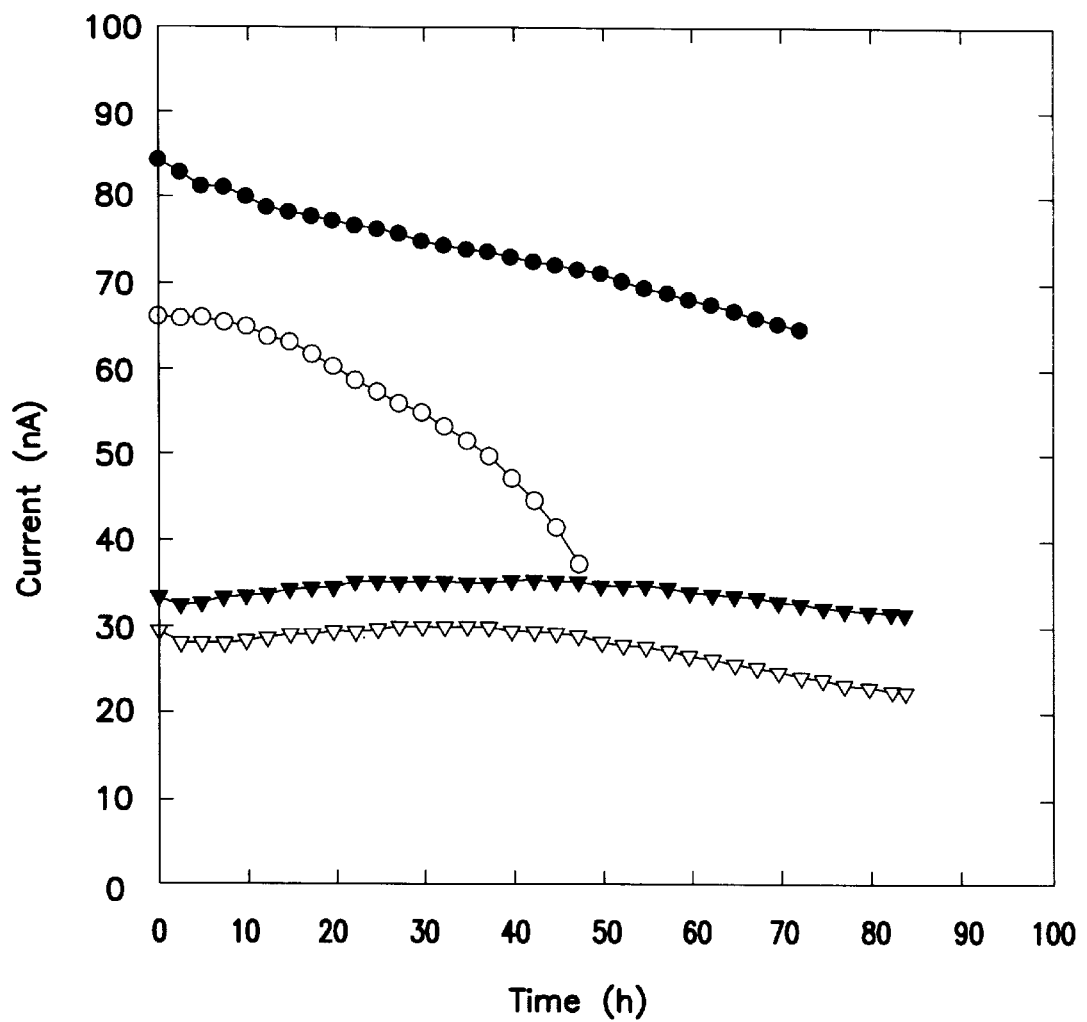
FIG. 5 is a graphical representation of data generated comparing variation of current generated by electrodes having sensing layers of differing thickness and diffusion limiting layers of different compositions and thickness. Solid circles: 7.5 $\mu$m thick sensing layer of PVI$_5$-Os (52%), rGOX (35%), PEGDGE (13%), coated with 4 $\mu$m PAL/PAZ (1:1 ratio). Open circles: 5.0 sensing layer. Solid triangles: 12.5 $\mu$m sensing layer and 7 $\mu$m PAL/PAZ (1:2 ratio). Open triangles: 7.5 $\mu$m sensing layer and 4.5 $\mu$m PAL/PAZ (1:2 ratio).

As expected, and as can be seen in FIG. 5, with thinner films the glucose mass transport was increased, i.e., the current was higher, while for thicker films the stability was improved. Because of the high sensitivity of thin sensing film (approximately 1 μm) electrodes (less than $10^{-2} A\, cm^{-2}\, M^{-1}$), an order of magnitude decrease in sensitivity could be traded for stability, while the currents remained high enough to be easily measured.

As seen in FIG. 5, the sensitivity of the stabilized sensors does not change by more than ±5% for 72 hours of operation at 37° C. After a small initial decrease in sensitivity, it increased to a maximum after 40 hours and the final 72 hour sensitivity was almost identical with the initial.

The characteristics of the electrodes of the present invention are summarized in Table 1. Each entry represents an average value for five tested electrodes. Baseline currents are typically less than 0.5 nA and the noise less than 10 pA. The currents observed throughout the physiological glucose concentration range (2–20 mM) exceed the noise equivalent current by at least a factor of 100. The apparent $K_m$ is 20 mm, and the 10% to 90% response time is, for aged electrodes, about 90 seconds at the lowest physiologically relevant glucose concentration (2 mM) and 20 seconds at the highest (20 mM).

The baseline of nil at 0 mM glucose is stable for 36 hours in the presence of 0.1 mM ascorbate. The stability observed and the existence of a valid zero-point in the presence of interferants suggest that the sensor can be used in vivo for 72 hours and tested/recalibrated in vivo through a single point calibration, i.e., by withdrawing only a single sample of blood for independent analysis.

TABLE 1

SENSOR CHARACTERISTICS

| i(nA) | J(μA/cm²) | $K_M^{app}$(mM) EH | $K_M^{app}$(mM) LB | $t_r$(s) | Current Variance (%) |
|---|---|---|---|---|---|
| 33.9 | 69.1 | 18.5 | 33.4 | 30–90 | 5.0 | where:
- i is the current measured at 37° C. and at 10 mM glucose concentration
- j is the current density measured at 37° C. at 10 mM glucose concentration
- $K_m^{app}$ is the apparent Michaelis-Menten coefficient determined from an electrochemical Eadie-Hoffstee (EH) or Lineweaver-Burk (LB) plot
- $t_r$ is the 10–90% risetime, 90 s for 2 mM and 30 s for 20 mH glucose concentration.
- Current Variance is the maximum deviation from the mean value, measured during the 72 hour test, conducted in 10 mM glucose in the presence of interferants. The current was continuously monitored at 37° C.

The foregoing examples are designed to illustrate certain aspects of the present invention. The examples are not intended to be comprehensive of all features and all embodiments of the present invention, and should not be construed as limiting the claims presented herein.

We claim:

1. A method of using an analyte-responsive electrochemical sensor, the method comprising steps of:
   (a) implanting an analyte-responsive electrochemical sensor into a patient;
   (b) determining, using a device other than the analyte-responsive electrochemical sensor, at least one analyte concentration value for the patient to generate a single calibration value;
   (c) obtaining an output signal related to the analyte concentration from the analyte-responsive electrochemical sensor; and
   (d) correlating the calibration value to the output signal to provide a single point, in vivo calibration of the electrochemical sensor.

2. The method of claim 1 wherein the correlating step comprises correlating the calibration value to the output signal to provide a single point, in vivo calibration that is based on a linear relationship between the output signal of the electrochemical sensor and the analyte concentration.

3. The method of claim 1 wherein the step of obtaining an output signal related to the analyte concentration from the analyte-responsive electrochemical sensor comprises intermittently obtaining an output signal related to the analyte concentration from the analyte-responsive electrochemical sensor.

4. The method of claim 1 wherein the step of obtaining an output signal related to the analyte concentration from the analyte-responsive electrochemical sensor comprises continuously obtaining an output signal related to the analyte concentration from the analyte-responsive electrochemical sensor.

5. The method of claim 1 wherein the analyte-responsive electrochemical sensor generates a baseline current of less than 0.5 nA.

6. The method of claim 1 wherein the step of correlating the calibration value to the output signal to provide a single point, in vivo calibration of the electrochemical sensor comprises correlating the calibration value to the output signal using a baseline of approximately nil at 0 mM analyte.

7. The method of claim 1 wherein the step of correlating the calibration value to the output signal to provide a single point, in vivo calibration of the electrochemical sensor comprises correlating the calibration value to the output signal using a baseline current of less than 0.5 nA at 0 mM analyte.

8. A method of using an analyte-responsive electrochemical sensor, the method comprising steps of:
   (a) implanting an analyte-responsive electrochemical sensor into a patient, the analyte-responsive electrochemical sensor comprising:
      (i) at least one non-corroding electrode; and
      (ii) a sensing layer disposed over the electrode;
   (b) determining, using a device other than the analyte-responsive electrochemical sensor, at least one analyte concentration value for the patient to generate a single calibration value;
   (c) obtaining an output signal related to the analyte concentration from the analyte-responsive electrochemical sensor; and
   (d) correlating the calibration value to the output signal to provide a single point, in vivo calibration of the electrochemical sensor.

9. The method of claim 8 wherein the analyte-responsive electrochemical sensor further comprises an analyte flux limiting layer disposed over the sensing layer.

10. The method of claim 9 wherein the analyte flux limiting layer comprises an electrically insulating polymer.

11. The method of claim 8 wherein the analyte-responsive electrochemical sensor further comprises an interferant eliminating layer disposed over the sensing layer.

12. The method of claim 11 wherein the interferant eliminating layer comprises a peroxidase.

13. The method of claim 12 wherein the interferant eliminating layer further comprises lactate oxidase.

14. The method of claim 8 wherein the analyte-responsive electrochemical sensor further comprises a biocompatible layer disposed over the sensing layer.

15. The method of claim 14 wherein the biocompatible layer comprises a hydrogel.

16. The method of claim 8 wherein the sensing layer comprises an analyte-responsive enzyme.

17. The method of claim 8 wherein the sensing layer comprises a non-leachable redox mediator.

18. A method of using a glucose-responsive electrochemical sensor, the method comprising steps of:
  (a) implanting a glucose-responsive electrochemical sensor into a patient, the glucose-responsive electrochemical sensor comprising:
    (i) at least one non-corroding electrode;
    (ii) a sensing layer disposed over the electrode, the sensing layer comprising a glucose-responsive enzyme; and
    (iii) an interferant eliminating layer disposed over the sensing layer;
  (b) determining, using a device other than the glucose-responsive electrochemical sensor, at least one glucose concentration value for the patient to generate a single calibration value;
  (c) obtaining an output signal related to the glucose concentration from the glucose-responsive electrochemical sensor; and
  (d) correlating the calibration value to the output signal to provide a single point, in vivo calibration of the electrochemical sensor.

19. A method of using an analyte-responsive electrochemical sensor, the method comprising steps of:
  (a) implanting an analyte-responsive electrochemical sensor into a patient;
  (b) assaying a body fluid of the patient, using a device other than the analyte-responsive electrochemical sensor, to obtain at least one analyte concentration value for the patient, and generating a single calibration value from the at least one analyte concentration value;
  (c) obtaining an output signal related to the analyte concentration from the anaylte-responsive electrochemical sensor; and
  (d) correlating the calibration value to the output signal to provide a linear calibration curve based on a single point, in vivo calibration of the electrochemical sensor.

20. A method of using a glucose-responsive electrochemical sensor, the method comprising steps of:
  (a) subcutaneously implanting a glucose-responsive electrochemical sensor into a patient;
  (b) determining, using a device other than the glucose-responsive electrochemical sensor, a calibration value;
  (c) obtaining an output signal related to the glucose concentration from the glucose-responsive electrochemical sensor; and
  (d) correlating the calibration value to the output signal to provide a calibration of the electrochemical sensor based on a fixed baseline value at 0 mM glucose.

21. The method of claim 20 wherein the step of determining, using a device other than the glucose-responsive electrochemical sensor, a calibration value comprises determining a single calibration value.

22. The method of claim 20 wherein the step of obtaining an output signal comprises obtaining a plurality of output signals from the glucose-responsive electrochemical sensor, and wherein the correlating step comprises, after obtaining the plurality of output signals, correlating the calibration value to one or more of the output signals obtained at approximately the same time as the calibration value to provide a calibration of the electrochemical sensor for at least the plurality of output signals.

23. The method of claim 20 wherein the sensor comprises at least one working electrode, the at least one working electrode comprising an glucose-responsive sensing layer disposed thereon.

24. The method of claim 23, wherein the sensing layer comprises a non-leachable redox mediator.

25. The method of claim 23, wherein the sensing layer comprises a glucose-responsive enzyme.

26. The method of claim 25, wherein the glucose-responsive enzyme comprises glucose oxidase, glucose dehydrogenase, or mixtures thereof.

27. The method of claim 25, wherein the glucose-responsive enzyme is non-leachable.

28. The method of claim 23, wherein at least one working electrode further comprises a barrier layer disposed over the sensing layer to at least slow a rate of permeation of interferents.

29. The method of claim 28, wherein the barrier layer comprises a polyanionic polymer.

30. The method of claim 23, wherein at least one working electrode further comprises an interferent eliminating layer disposed over the sensing layer.

31. The method of claim 30, wherein the interferent eliminating layer comprises a peroxide-generating enzyme.

32. The method of claim 23, wherein at least one working electrode further comprises, disposed over the sensing layer, a glucose flux limiting layer to limit diffusion of glucose.

33. The method of claim 23, wherein at least one working electrode further comprises a biocompatible layer disposed over the sensing layer.

34. The method of claim 33, wherein the biocompatible layer is bound to the sensing layer.

35. The method of claim 34, wherein the biocompatible layer is indirectly bound to the sensing layer via an intermediate layer between the biocompatible layer and the sensing layer.

36. The method of claim 35, wherein the intermediate layer comprises at least one of an interferent eliminating layer and a glucose flux limiting layer.

37. The method of claim 34, wherein the biocompatible layer is chemically bound to the sensing layer.

38. The method of claim 34, wherein the biocompatible layer is crosslinked with the sensing layer.

39. The method of claim 33, wherein the biocompatible layer comprises a hydrogel.

40. The method of claim 33, wherein the biocompatible layer comprises at least one material selected from the group consisting of hydrophilic polyurethanes, poly(vinyl alcohol), and polyHEMA membranes.

41. The method of claim 33, wherein the biocompatible layer comprises polyethylene oxide.

42. The method of claim 23, wherein at least one working electrode is configured and arranged to provide a substantially constant signal output in absence of glucose.

43. The method of claim 23, wherein at least one working electrode is configured and arranged to have a baseline current of less than 0.5 nA in absence of glucose.

44. The method of claim 23, wherein at least one working electrode is configured and arranged to have a noise level of less than 10 pA.

45. The method of claim 23, wherein at least one working electrode is configured and arranged to generate a signal of at least 3 nA at 2 mM glucose.

46. The method of claim 23, wherein the glucose-responsive sensing layer defines, on the working electrode, a working surface having an area of no more than 0.05 mm$^2$.

47. The method of claim 23, wherein correlating the calibration value comprises correlating the calibration value to the output signals generated by at least two working electrodes of the electrochemical sensor.

48. The method of claim 47, further comprising comparing signals generated at each of the working electrodes and accepting those signals that do not differ by more than a predetermined degree.

49. The method of claim 20, further comprising disposing a reference or counter/reference electrode on the skin of the animal.

* * * * *

UNITED STATES PATENT AND TRADEMARK OFFICE
CERTIFICATE OF CORRECTION

PATENT NO.    : 6,162,611
DATED         : December 19, 2000
INVENTOR(S)   : Heller et al.

It is certified that error appears in the above-identified patent and that said Letters Patent is hereby corrected as shown below:

Title page,
Item [63], Related U.S. Application Data, delete ", and a continuation-in-part of application No. 08/161,682, Dec. 2, 1993, Pat. No. 5,356,786"
Item [56], References Cited, U.S. PATENT DOCUMENTS, "4,241,438" should read -- 4,240,438 --, and "5,496,772" should read -- 5,497,772 --

Column 1,
Line 9, delete "This is a continuation in part of copending U.S. patent application Ser. No. 08/161,682, filed Dec. 2, 1993 now U.S. Pat. No. 5,356,786, which is hereby incorporated by reference for all purposes."

Column 4,
Line 23, "diameter a" should read -- diameter $a$ --
Line 24, "diameter b" should read -- diameter $b$ --
Line 28, "length c" should read -- length $c$ --.

Column 5,
Line 16, "lose" should read -- less --
Line 18, "gold, an be" should read -- gold, can be --

Column 8,
Line 14, "sensor. it is" should read -- sensor. It is --

Column 9,
Line 34, "two a," should read -- two $\alpha$, --

UNITED STATES PATENT AND TRADEMARK OFFICE
CERTIFICATE OF CORRECTION

PATENT NO.    : 6,162,611
DATED         : December 19, 2000
INVENTOR(S)   : Heller et al.

It is certified that error appears in the above-identified patent and that said Letters Patent is hereby corrected as shown below:

Column 11,
Line 53, "depth c" should read -- depth $c$ --

Signed and Sealed this

Eleventh Day of November, 2003

JAMES E. ROGAN
*Director of the United States Patent and Trademark Office*